(12) United States Patent
Chen et al.

(10) Patent No.: US 7,968,711 B2
(45) Date of Patent: Jun. 28, 2011

(54) ABNORMAL CANNABIDIOLS AS AGENTS FOR LOWERING INTRAOCULAR PRESSURE

(75) Inventors: June Chen, San Juan Capistrano, CA (US); Simon N. Pettit, Essex (GB); Hans G. Fliri, Saffron Walden (GB)

(73) Assignee: Allergan, Inc., Irvine, CA (US)

( * ) Notice: Subject to any disclaimer, the term of this patent is extended or adjusted under 35 U.S.C. 154(b) by 14 days.

(21) Appl. No.: 11/739,183

(22) Filed: Apr. 24, 2007

(65) Prior Publication Data

US 2007/0249596 A1 Oct. 25, 2007

Related U.S. Application Data

(63) Continuation-in-part of application No. 11/409,868, filed on Apr. 24, 2006, and a continuation-in-part of application No. 11/409,570, filed on Apr. 24, 2006, and a continuation-in-part of application No. 11/409,871, filed on Apr. 24, 2006.

(51) Int. Cl.
*C07D 401/00* (2006.01)
*C07D 237/00* (2006.01)
*C07D 237/02* (2006.01)
*C07D 405/00* (2006.01)

(52) U.S. Cl. ......... 544/238; 544/240; 544/241; 546/210

(58) Field of Classification Search .................. 544/238, 544/240, 241; 546/210
See application file for complete search history.

(56) References Cited

U.S. PATENT DOCUMENTS

| 3,281,424 A | 10/1966 | Doebel et al. |
|---|---|---|
| 2002/0137961 A1 | 9/2002 | Bradley et al. |
| 2002/0161041 A1 | 10/2002 | Browning et al. |
| 2003/0180234 A1 | 9/2003 | Love et al. |
| 2005/0282902 A1 | 12/2005 | Chen et al. |
| 2005/0282912 A1 | 12/2005 | Chen et al. |
| 2005/0282913 A1 | 12/2005 | Chen et al. |

FOREIGN PATENT DOCUMENTS

| EP | 0119087 | 9/1984 |
|---|---|---|
| EP | 0 210 647 | 7/1986 |
| EP | 0492904 | 7/1992 |
| FR | 1384304 | 11/1964 |
| GB | 917849 | 2/1963 |
| WO | WO03/068230 | 8/2003 |
| WO | WO 03/091189 | 11/2003 |
| WO | WO 2005/007632 | 1/2005 |
| WO | WO2005/007632 | * 1/2005 |
| WO | WO 2006/001982 | 1/2006 |
| WO | WO 2006/007227 | 1/2006 |
| WO | WO 2007/008548 | 1/2007 |
| WO | WO2007/014226 | * 1/2007 |
| WO | WO2007/014226 | 2/2007 |

OTHER PUBLICATIONS

Wei-dong Liu, et al, Synthesis and Biological Activity of Methyl N-methoxy-N-[2-substituent-4-chloro-3(2H)-pyridazinone-5-yl-oxymethyl (or mercaptomethyl)phenyl] carbamates, 13 Hecheng Huaxue 33 (2005).*
Lidia Moreira Lima & Eliezer J. Barreiro, Bioisosterism: A Useful Strategy for Molecular Modification and Drug Design, 12 Curr. Med. Chem. 23 (2005).*
V. Konecny, Pyridazinones. I. Preparation of 2,4-disubstituted 5-hydroxy-3(2H)-pyridazinones and 2,5-disubstituted 4-hydroxy-3(2H)-pyridazinones, 30 Chem. Zvesti. 663, 664-69 (1975).*
J. Zuziova, et al, Synthesis and Pesticidal Activity of 2,4-disubstituted O-(haloalkyl)-O-(alkyl, Aryl)-(N-Alkylamido, N,N-dialkylamido)-O-(3-oxo-2H-pyridazine-5-yl) Esters of Thiophosphoric Acid, 42 Chem. Papers. 415 (1988).*
Yoshifumi Maki & Masahiko Takaya, The Ring Contraction of Pyridazinones to Pyrazoles, 19 Chem. Pharm. Bull. 1635, 1638 (1971).*
V. Konecny, Pyridazinones. I. Preparation of 2,4-disubstituted 5-hydroxy-3(2H)-pyridazinones and 2,5-disubstituted 4-hydroxy-3(2H)-pyridazinones, 30 Chem. Zvesti. 663, 664-69 (1975).*
Yoshifumi Maki & Masahiko Takaya, The Ring Contraction of Pyridazinones to Pyrazoles, 19 Chem. Pharm. Bull. 1635, 1638 (1971).*
Kd. Meier, et al, Chemotherapeutic Studies in the Heterocyclic Series. VII. Pyridazines. 4. Derivatives of Cyclic Chloromaleic Phenylhydrazides, 37 Helv. Chim. Acta .523 (1954).*
Wei-dong Liu, et al, Synthesis and Biological Activity of Methyl N-methoxy-N-[2-substituent-4-chloro-3(2H)-pyridazinone-5-yl-oxymethyl (or mercaptomethyl)phenyl] carbamates, 13 Hecheng Huaxue 33 (2005).* Lidia Moreira Lima & Eliezer J. Barreiro, Bioisosterism: A Useful Strategy for Molecular Modification and Drug Design, 12 Curr. Med. Chem. 23 (2005).*
Pisanenko et al, "Anti Microbial Activity of Cyclo Alkenyl Phenos and 4-Alpha Arylcyclopentyl Phenols", Pharmaceutical Chemistry Journal, vol. 10, No. 10, 1997.
Adams et al, "Structure of Cannabidiol. IV. The position of the linkage between the two rings", J. Am. Chem. Soc., vol. 62, pp. 1774-1775, 1940.

(Continued)

*Primary Examiner* — Jeffrey S Lundgren
*Assistant Examiner* — Sean Basquill
(74) *Attorney, Agent, or Firm* — Joel B. German; Debra D. Condino; Allergan, Inc.

(57) ABSTRACT

The present invention provides a method of treating glaucoma or ocular hypertension which comprises applying to the eye of a person in need thereof an amount sufficient to treat glaucoma or ocular hypertension of a compound of formula I

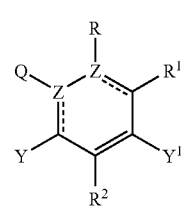

wherein Y, Q, Z, R, $R^1$ and $R^2$ are as defined in the specification.

The present invention further comprises pharmaceutical compositions, e.g. ophthalmic compositions, including said compound.

29 Claims, 5 Drawing Sheets

OTHER PUBLICATIONS

Fujikawa et al, Antiseptics for foods. LXXIII. 3-Halo-4-hydroxy benzoic acid esters, 4-alkylresorcinol, 4-arylresorcinol, . . . , Chemical Abstracts Database, XP00244503, 1972.

Arnoldi et al, "Analogues of Cannabinoids, Synthesis of N-Heterocyclic Derivatives of Olivetol", J. Chem., XP009087450, 1983.

Yorio et al, "New therapies for glaucoma: Are they all up to the task?", Expert Opinion on Therapeutic Patents 2004, vol. 14, No. 12, pp. 1743-1762, 2004.

Howlett et al, "International Union of Pharmacology. XXVII. Classification of Cannabinoid Receptors", Pharmacological Reviews, 54: 2002, pp. 161-202.

Cieplak et al, "Reversal of π-Facial Diastereoselection upon Electronegative Substitution of the Substrate and the Reagent", J. Am. Chem. Society, 1989, 111, pp. 8447-8462.

Micovic et al, "The synthesis of lactam analogues of fentanyl", J. Chem. Soc., Perkin Trans 1, 1996, pp. 2041-2050.

Wagner et al, "Mesenteric Vasodilation Mediated by Endothelial Anandamide Receptors", Hypertension. 33 [part II], 1999, pp. 429-434.

Jarai et al, Cannabinoid-induced mesenteric vasodilation through an endothelial site distinct from CB1 or CB2 receptors, PNAS, vol. 96, No. 24, 1999, pp. 14136-14141.

McNamara et al, "Synthesis, antitumor activity, and antiviral activity of 3-substituted 3-deazacytidines and 3-substituted 3-deazauridines", Journal of Medicinal Chemistry, vol. 33, No. 7, pp. 2006-2011, 1990.

Katz et al, "Synthesis of pyridazine analogues of the naturally occurring nucleosides cytidine, uridine, deoxycytidine, and deoxyuridine", Journal of Medicinal Chemistry, vol. 25, No. 7, pp. 812-821, 1982.

Konecny et al, "Synthesis, Spectral Properties, and Pesticidal Activity of 4-Amino(Alkylamino, Dialkylamino)-5-Chloro-2-Substituted-3-Oxo-2H-Pyr Idazines and 5-Amino(Alkylamino, Dialkylamino)-4-Chloro-2-Substituted 3-Oxo-2H-Pyridazines", Collection of Czechoslovak Chemical Communications, pp. 492-502, 1985.

Schober et al, "Pyridazines with heteroatom substituents in positions 3 and 5.6 SN Reactions in position 5 of 2-aryl-5-hydroxypridazin-3(2H)-ones", Journal of Heterocyclic Chemistry, vol. 27, No. 3, pp. 471-477, 1990.

McElvan et al, "Ketene Acetals. XII. The reaction of ketene diethylacetal with diazonium salts", Journal of the American Chemical Society, p. 2238, 1943.

Konecny, "Pyridazinones. I. Preparation of 2, 4-disubstituted 5-hydroxy-3(2H)-pyridazinones and 2,5-disubstituted 4-hydroxy-3(2H)-pyridazinones", Chemick Zvesti-Chemical Papers, vol. 30, pp. 663-673, 1976.

Liu et al, "Synthesis and biological activity of methyl N-methoxy-N-[2-substituent-4-chloro-3(2H)-pyridazinone-5-yl-oxymethyl(or mercaptomethyl)phenyl]carbamates", Database accession No. 2005-274821, 2005.

Zuziova et al, "Synthesis and pesticidal activity of 2,4-disubstituted 0-(haloalkyl)-O-(alkyl, aryl)-(N-alkylamido, N,N-dialkylamido)-)-(3-oxo-2H-pyridazine-5-yl)esters of thiophospornic acid", Database accession No. 1989:114966.

Baloniak et al, "Synthesis of the derivatives of 1-(2-and 3-methylphenyl)-3-hydroxy-6-pyridazinones", Database accession No. 1983:453681.

Miyake et al, "Pyridazinone Derivative andController Against Insect Pest", Database accession No. 118957-78-1, 1988.

Cho et al, "Novel synthesis of pyridazino[4,5-b][1,4]oxazin-3,8-diones", Tetrahedron Letters, vol. 44,No. 50, 2003.

Bekhli et al, "Structure of the products of the cyclization in actic anhydride of ?-(2-carboxy-5-chlorophyenylamino)propionic acid andits nitrile", Chmistry of Heterocyclic Compounds, vol. 6, No. 7, pp. 814-819, 1970.

Asahi et al, "Manganese(III)-based oxidation of 2,4-piperidinediones in the presence of alkenes", Tetrahedron, vol. 61, No. 47, pp. 11107-11124, 2005.

Micovic et al, "The Synthesis of Lactam Analogues of Fentanyl", Journal of the Chemistry Society, pp. 2041-2050, 1996.

Gegner, "Synthesis of 1-phenyl-3-3thy1-4-hydroxy-2(1H)-pyridone", Tetrahedron Letters, pp. 287-8, 1969.

Tomisawa, "1-Alkyl-2-pyridone derivatives I. Sandmyer reaction of 1-phenethyl-4(or 5)-amino-2-pyridone", Database accession 1960:16966.

Hirohashi et al, "Synthesis of 5-fluorouracil derivatives containing an inhibitorof 5-fluorouracil degradation", Chemical and Pharmaceutical Bulletin, vol. 41, No. 9, pp. 1498-1506, 1993.

\* cited by examiner

ABNORMAL CANNABIDIOLS AS AGENTS FOR LOWERING INTRAOCULAR PRESSURE

CROSS REFERENCE TO RELATED APPLICATIONS

This is a Continuation-In-Part (CIP) based on, and claims the benefit of U.S. Ser. No. 11/409,868 filed Apr. 24, 2006; Ser. No. 11/409,570 filed Apr. 24, 2006, and Ser. No. 11/409,871 filed Apr. 24, 2006, and which are incorporated herein by reference.

BACKGROUND OF THE INVENTION

1. Field of the Invention

The present invention relates to the use of Abnormal Cannabidiols to lower the intraocular pressure of mammals and thus are useful in treating glaucoma.

2. Background of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical α-adrenoreceptor antagonists have traditionally been the drugs of choice for treating glaucoma.

Certain Abnormal Cannabidiols are disclosed in Howlett et al, "International Union of Pharmacology. XXVII. Classification of Cannabinoid Receptors", Pharmacological Reviews 54: 161-202, 2002.

Reference is made to Published U.S. Patent Application Numbers 2005/0282902, 2005/0282912 and 2005/0282913 to Chen et al which were published on Dec. 22, 2005 and are herein incorporated by reference thereto. (June Chen is a co-inventor of each of said published patent applications and the present patent application.)

SUMMARY OF THE INVENTION

We have found that Abnormal Cannabidiols are potent ocular hypotensive agents. We have further found that Abnormal Cannabidiols and homologues and derivatives thereof, are especially useful in the treatment of glaucoma and surprisingly, cause no or significantly lower ocular surface hyperemia than the other compounds that are useful in lowering intraocular pressure, e.g. $PGF_{2\alpha}$ and lower alkyl esters thereof.

The present invention relates to methods of treating ocular hypertension which comprises administering an effective amount of a compound represented by

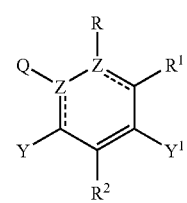

I wherein Y is selected from the group consisting of keto and hydroxyl;
$Y^1$ is selected from the group consisting of hydroxyl, keto, halogen and $C_1$-$C_5$ alkyl;
Z is N or C;
Q is selected from the group consisting of phenyl, halogen-substituted phenyl, 5 or 6 member heterocyclic radicals, wherein the hetero atom is nitrogen, oxygen or sulfur,

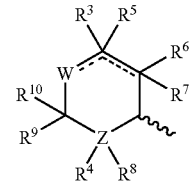

wherein W is a direct bond or $C(R^{11})(R^{12})$;
a dotted line represents the presence or absence of a double bond;
the wavy line represents a direct bond;
Q and Y may form a condensed ring wherein Y is —C(O)—NR3- and Q is —C(Q')- wherein Q' is R3 or said C is a spiro atom and Q', together with said C, represents a carbocyclic or heterocyclic ring having from 3 to 6 carbon atoms and said hetero atom is N, O or S;
R is selected from the group consisting of H, halogen and $C_{1-5}$ alkyl;
$R^1$ is selected from the group consisting of H and halogen;
$R^2$ is selected from the group consisting of H, $C_{1-5}$ alkyl, halogen, $XC_{1-5}$ alkyl, $C_{1-5}$ alkyl$OR^{13}$, $C_{1-5}$ alkyl$N(R^{13})_2$, $N(R^{13})_2$, $XC_{1-5}$ alkyl$N(R^{13})_2$ and $XC_{1-5}$ alkyl$OR^{13}$; wherein X is O or $S(O)_n$;
n is 0 or an integer of from 1 to 2;
$R^3$ is selected from the group consisting of H, hydroxyl, oxo, $C_{1-5}$ alkyl, $C_{1-5}$ alkyl$OR^{13}$ and $C_{1-5}$ alkyl$N(R^{13})_2$;

$R^4$ is selected from the group consisting of H, $C_{1-5}$ alkenyl, $C_{1-5}$ alkyl, $C_{1-5}$ alkylOR$^{13}$ and $C_{1-5}$ alkylN(R$^{13}$)$_2$;

$R^5$, $R^6$, $R^7$, $R^8$, $R^9$, $R^{10}$, $R^{11}$, $R^{12}$ are independently selected from the group consisting of H, $C_{1-5}$ alkyl, $C_{1-5}$ alkylOR$^{13}$ and OR$^{13}$; and $R^{13}$ is selected from the group consisting of H, $C_{1-5}$ alkyl and $C_{3-8}$ cyclic alkyl, or two $R^{13}$ groups, together with N, may form a cyclic ring such as a piperidine or morpholine ring; and provided that $R^8$ and $R^{12}$ may, together, form a cyclic ring, and $R^3$ and $R^5$ may, together, represent O, and when Q is menthadiene, $R^1$ and $R^2$ are H and Y is hydroxyl, R may not be H or alkyl.

Preferably, the compound of formula I is

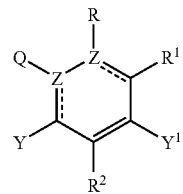

I' wherein Y is selected from the group consisting of keto and hydroxyl;

Z is N or C;

Q is selected from the group consisting of

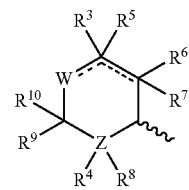

wherein W is a direct bond or C(R$^{11}$l)(R$^{12}$);

a dotted line represents the presence or absence of a double bond;

wherein R is selected from the group consisting of H, halogen, e.g. bromo or chloro; and $C_{1-5}$ alkyl; $R^1$ is selected from the group consisting of H, halogen, e.g. bromo or chloro;

$R^2$ is independently selected from the group consisting of H, $C_{1-5}$ alkyl, halogen, XC$_{1-5}$ alkyl, $C_{1-5}$ alkylOR$^{13}$, $C_{1-5}$ alkylN(R$^{13}$)$_2$, N(R$^{13}$)$_2$, XC$_{1-5}$ alkylN(R$^{13}$)$_2$ and XC$_{1-5}$ alkylOR$^{13}$;

X is O or S(O)$_n$;

n is 0 or an integer of from 1 to 2;

$R^3$ is selected from the group consisting of H, hydroxyl, $C_{1-5}$ alkyl, $C_{1-5}$ alkylOR$^{13}$ and $C_{1-5}$ alkylN(R$^{13}$)$_2$;

$R^4$ is selected from the group consisting of H, $C_{1-5}$ alkenyl, e.g. isopropenyl, $C_{1-5}$ alkyl, $C_{1-5}$ alkylOR$^{13}$ and $C_{1-5}$ alkylN(R$^{13}$)$_2$;

$R^5$, $R^6$, $R^7$, $R^8$, $R^9$, $R^{10}$, $R^{11}$, $R^{12}$ are independently selected from the group consisting of H, $C_{1-5}$ alkyl, $C_{1-5}$ alkylOR$^{13}$ and OR$^{13}$; and $R^{13}$ is selected from the group consisting of H, $C_{1-5}$ alkyl and $C_{3-8}$ cyclic alkyl, or two $R^{13}$ groups, together with N, may form a cyclic ring such as a piperidine or morpholine ring; and provided that any of said alkyl groups may be substituted with a hetero atom containing radical, wherein said heteroatom is $R^8$ and $R^{12}$ may, together, form a cyclic ring;

and $R^3$ and $R^5$ may, together, represent O, and when Q is menthadiene, $R^1$ and $R^2$ are H and Y is hydroxyl, R may not be H or alkyl.

In a further aspect, the present invention relates to pharmaceutical compositions comprising a therapeutically effective amount of a compound of formulae (I) or (I'), in admixture with an non-toxic, pharmaceutically acceptable liquid vehicle. Such pharmaceutical compositions may be ophthalmic solutions which are useful in treating ocular hypertension and/or glaucoma. Finally, the present invention provides certain novel compounds which are useful in treating ocular hypertension and/or glaucoma.

DETAILED DESCRIPTION OF THE INVENTION

Figure 1:
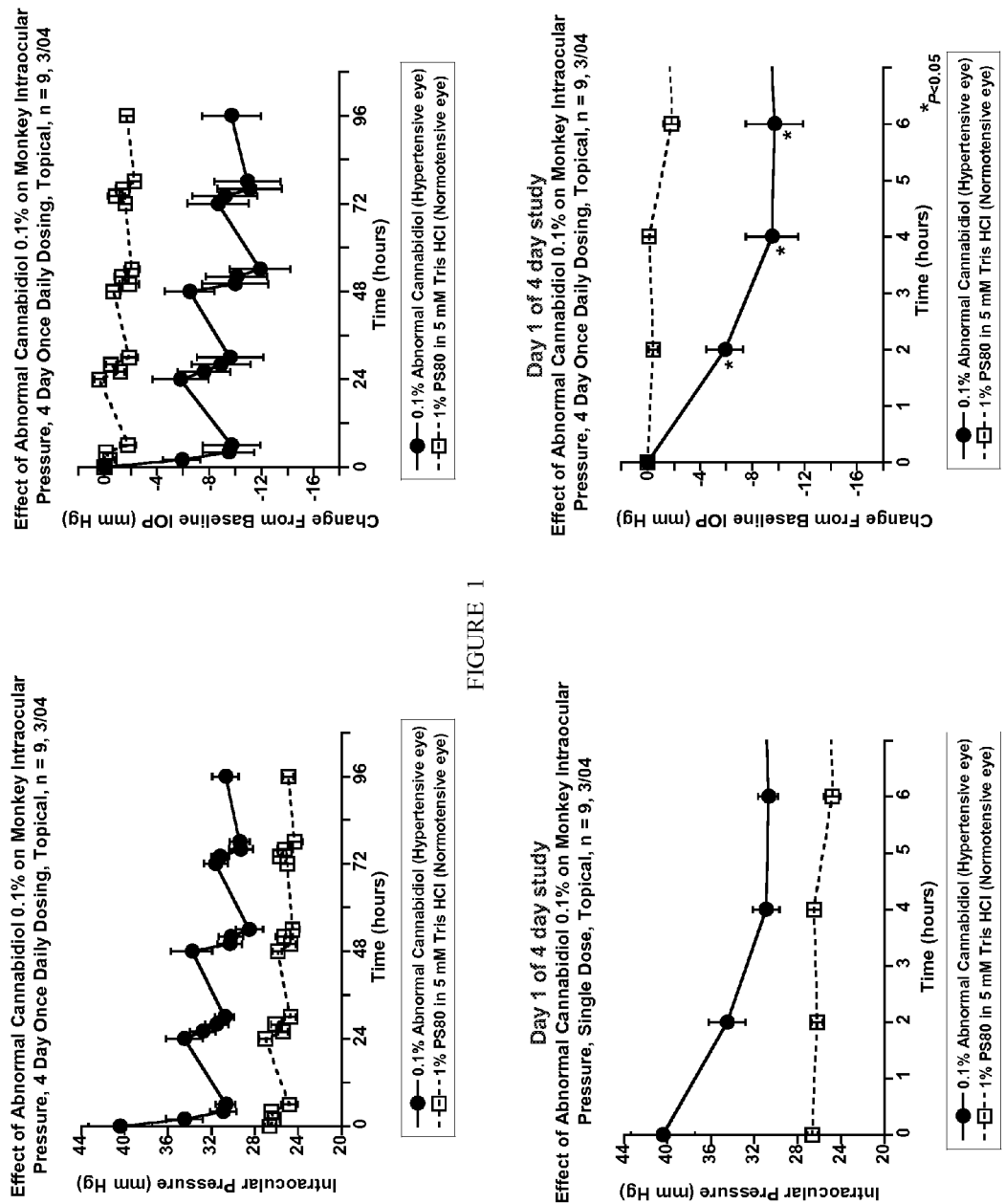
FIG. 1 shows the effect of abnormal cannabidiol on intraocular pressure.
Figure 2:
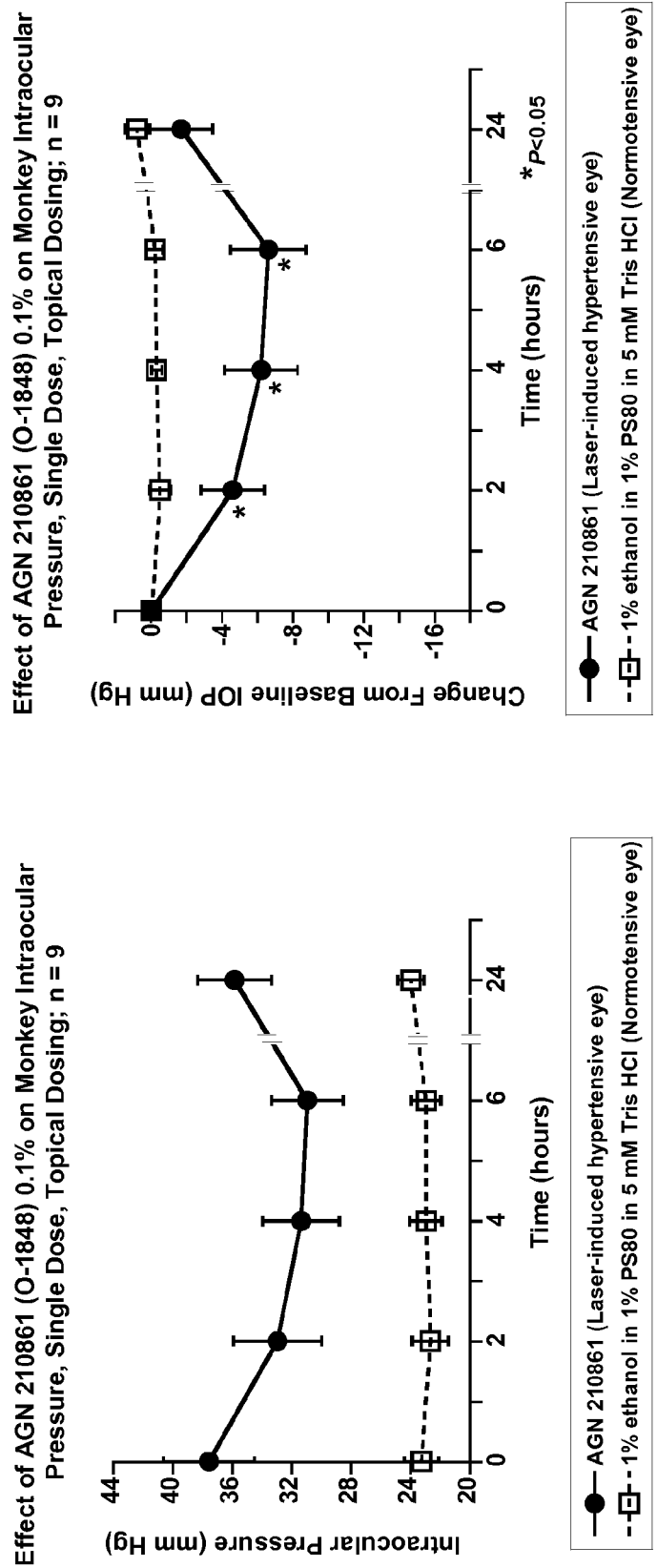
FIG. 2 shows the effect of the compound of Example 4 intraocular pressure.
Figure 3:
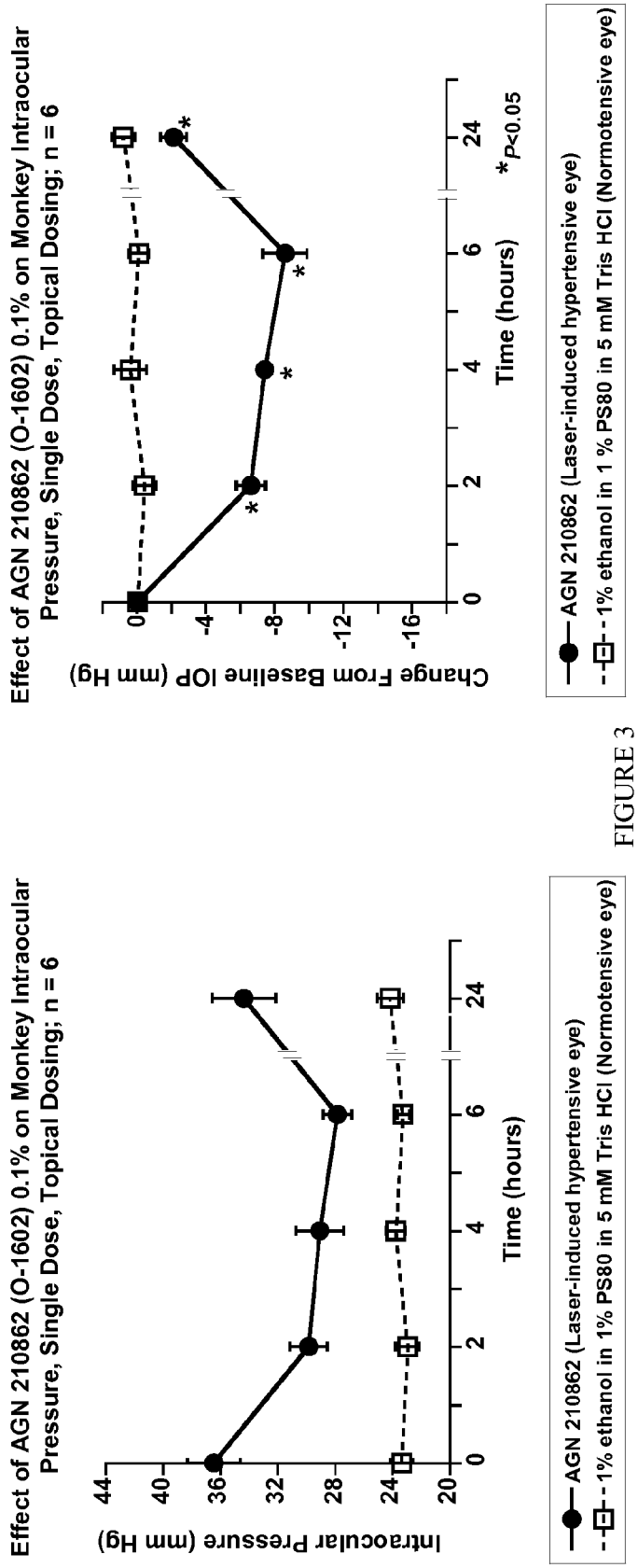
FIG. 3 shows the effect of the compound of Example 3 intraocular pressure.
Figure 4:
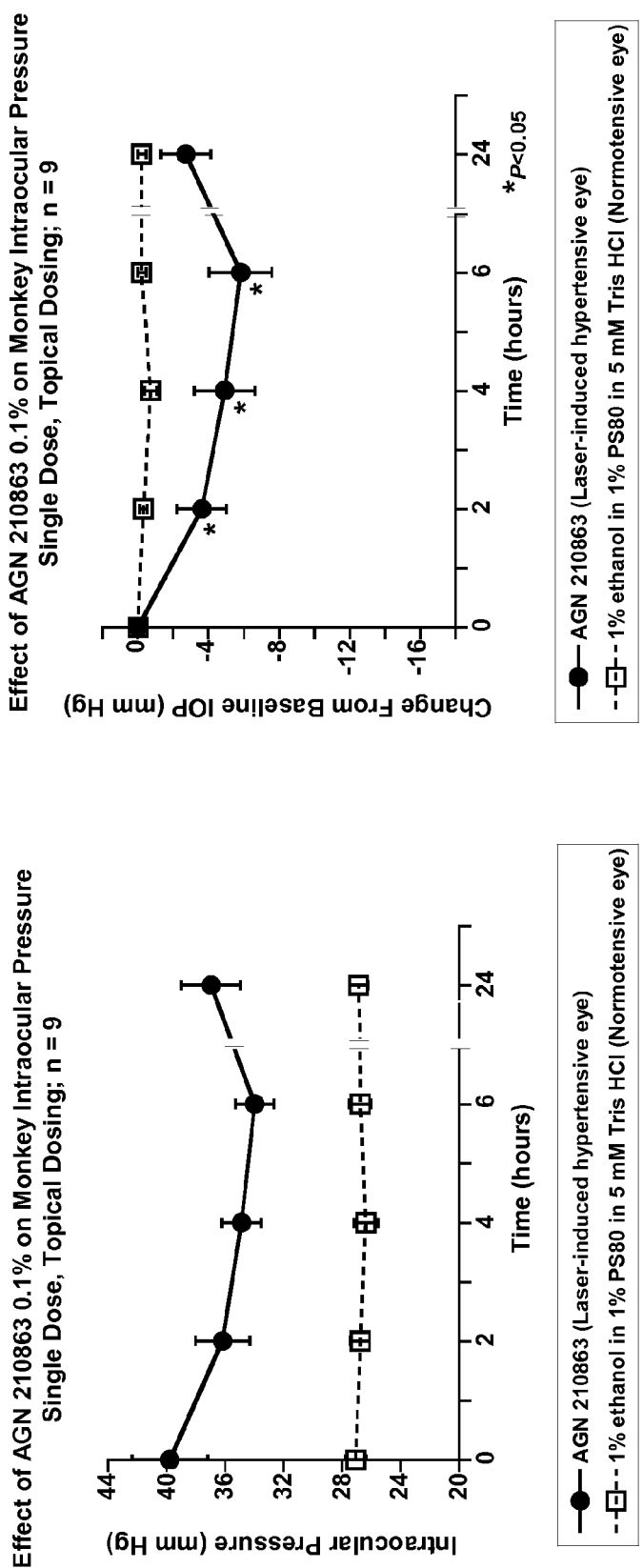
FIG. 4 shows the effect of the compound of Example 6 intraocular pressure.
Figure 5:
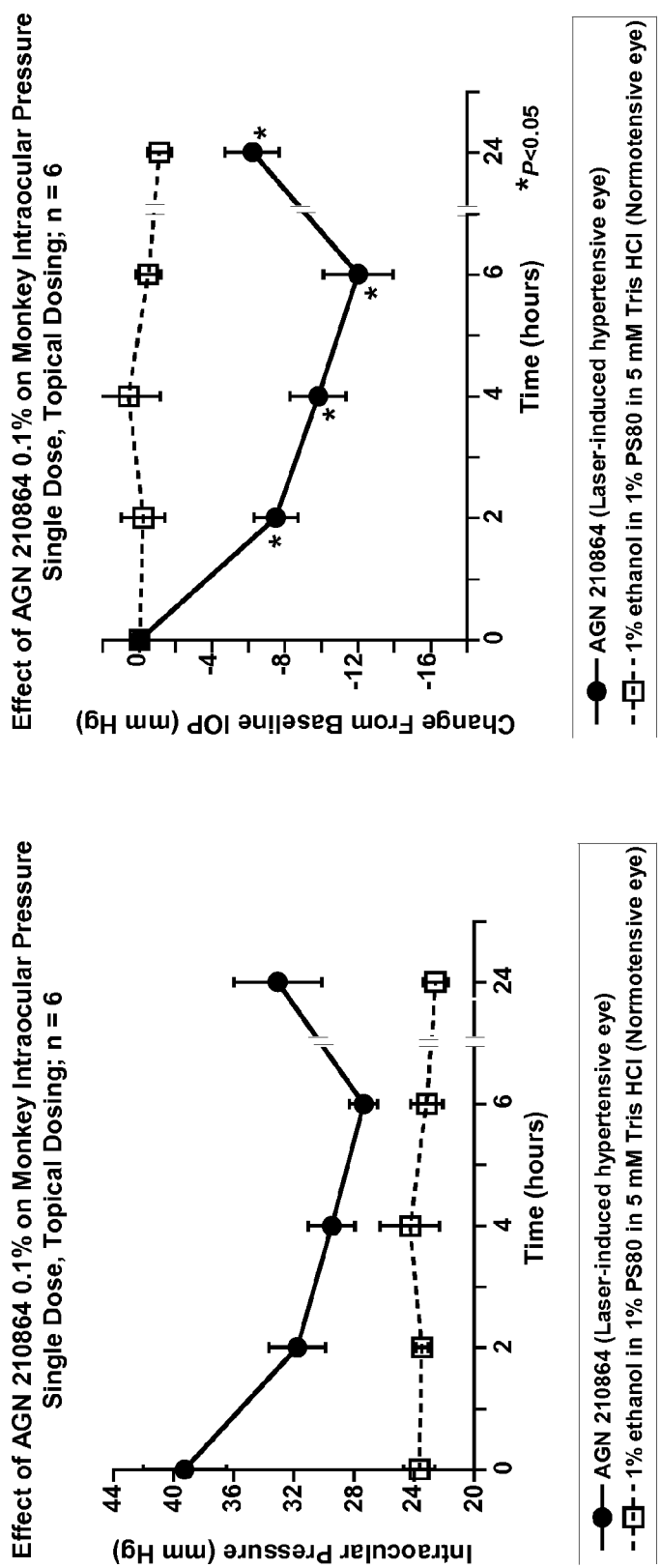
FIG. 5 shows the effect of the compound of Example 5 intraocular pressure.

The present invention relates to the use of Abnormal Cannabidiols as ocular hypotensives. These therapeutic agents are represented by compounds having the formula I or I', above.

In one embodiment of the invention, the compound is selected from the group consisting of abnormal Cannabidiols and analogues thereof represented by formula II

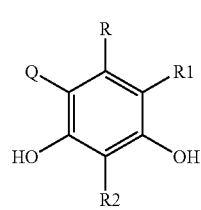

II wherein Q is selected from the group consisting of

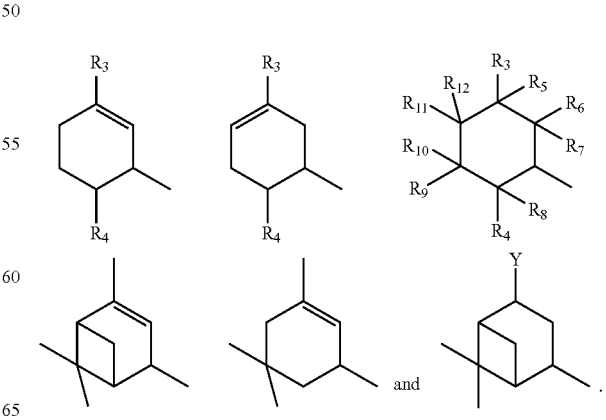

A particularly preferred group represented by Q is menthadiene or

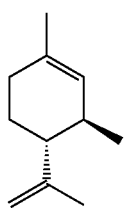

In this class of compounds, preferably, R is selected from the group consisting of hydrogen, methyl, bromo and chloro and $R^1$ is selected from the group consisting of hydrogen, methyl and chloro.

Compounds of this type may be prepared by condensation of a cyclic alkene or cyclic alcohol with a suitably substituted benzene-1,3-diol. The reaction is catalysed by an acid such as oxalic acid dihydrate or p-toluenesulphonic acid. The reaction is carried out in a solvent or mixture of solvents such as toluene, diethyl ether or dichloromethane. A mixture of the two isomers is obtained and the desired product is separated by chromatography. The reaction scheme is illustrated below.

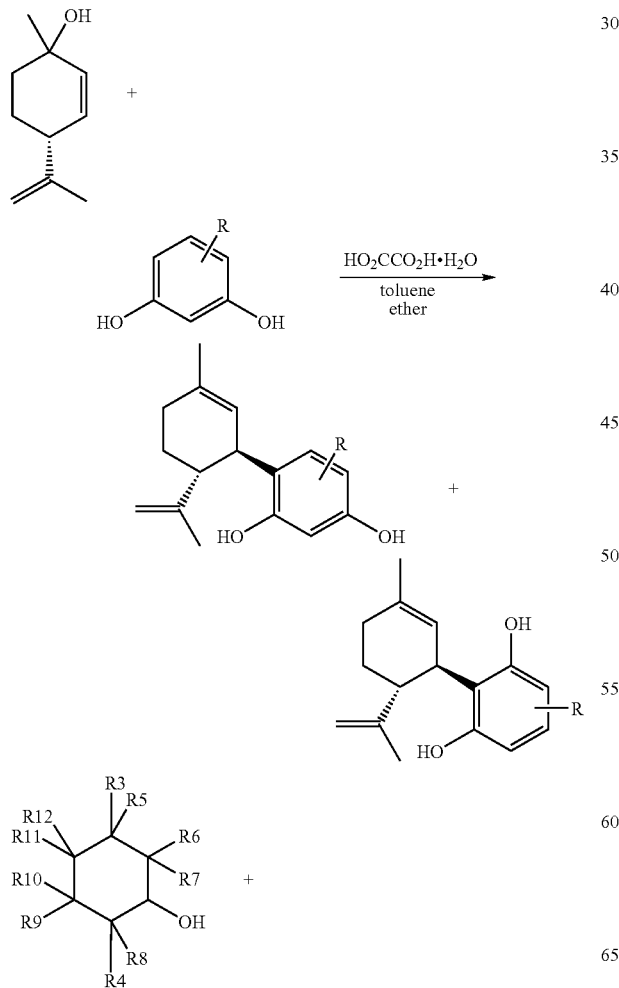

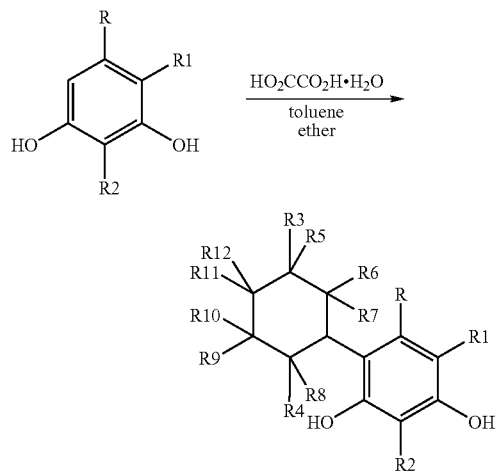

The synthesis of the starting materials is well known.

The mechanism of the reaction is the result of the formation of a carbocation by elimination of OH or a starting material containing a functional group such as acetate which can also be eliminated to give the carbocation can be used.

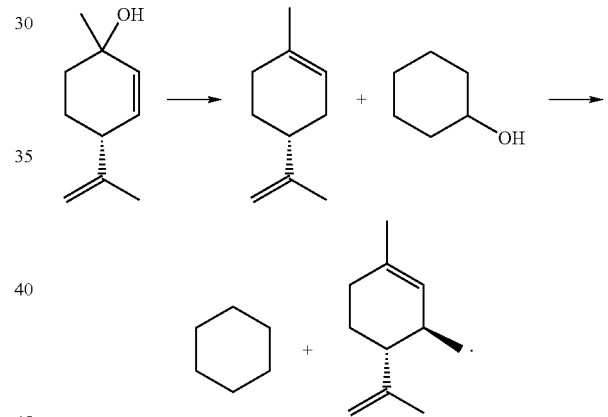

In another embodiment of the invention the compound is tetrahydropyridine represented by formula III

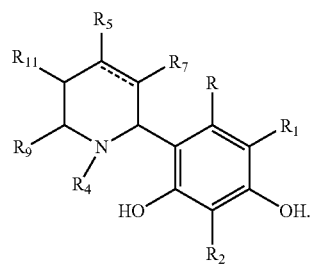

III

These tetrahydropyridine compounds may be synthesized according to the following reaction scheme wherein Me is methyl, Bu is butyl and iPr is isopropyl.

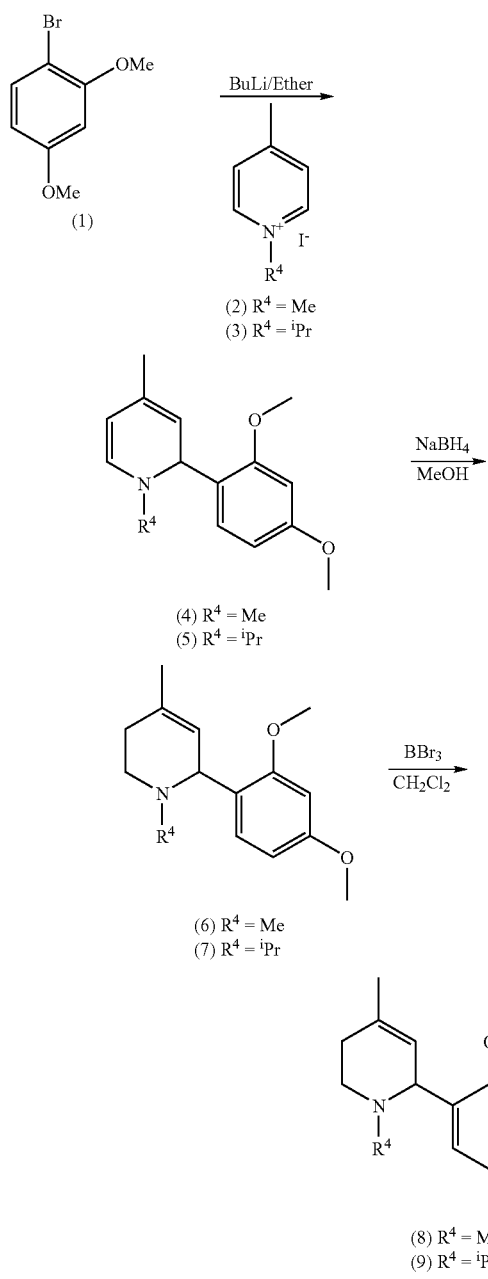

(2) $R^4$ = Me
(3) $R^4$ = $^i$Pr (4) $R^4$ = Me
(5) $R^4$ = $^i$Pr (6) $R^4$ = Me
(7) $R^4$ = $^i$Pr (8) $R^4$ = Me
(9) $R^4$ = $^i$Pr

In a further embodiment of the invention, the compound is a piperidinedione represented by the formula IV

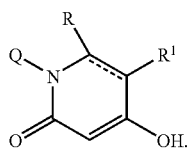

IV

These compounds may be synthesized according to the following reaction scheme wherein Et is ethyl, THF is tetrahydrofuran and DMF is dimethyl formamide.

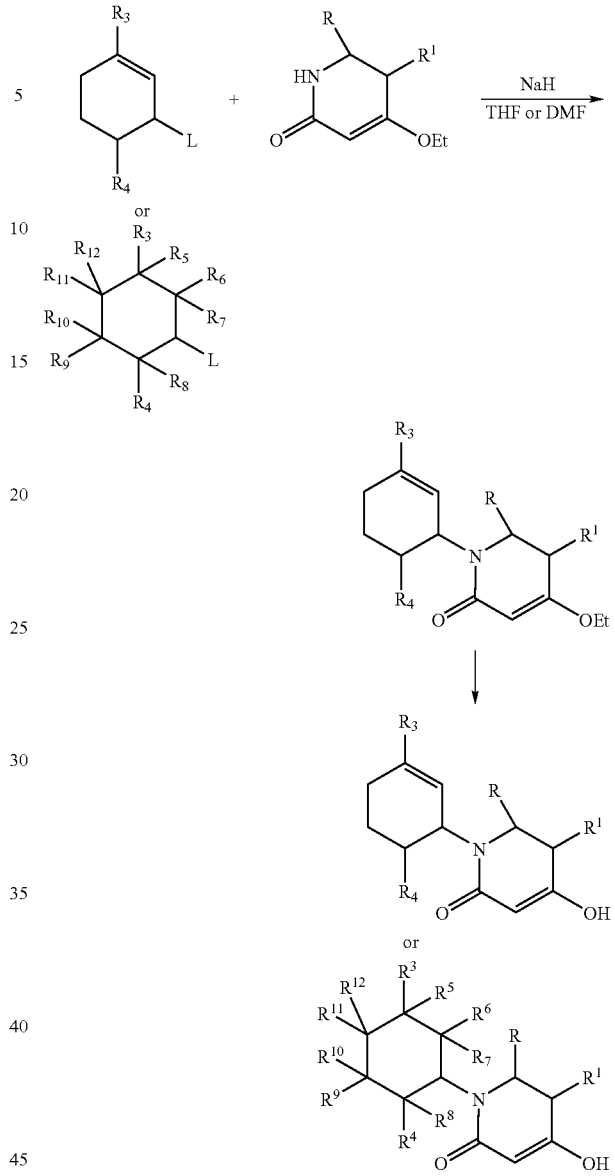

Where L is a leaving group such bromine, iodine or tosyl.

Compounds of formula I' wherein Y and $Y^1$ are keto are known as piperidine-2,4-diones and may be synthesized as described by H. Nishino, et al., Tetrahedron 2005, 11107-11124. The corresponding cyclohexane-1,3 diones may be prepared as described in EP 291114 and EP 310186. Compounds of formula I' wherein Y is keto and $Y^1$ is hydroxyl are known as 4-hydroxypyridin-2-ones and may be prepared as described by Castillo, et al. in Bull. Soc. Chim. Fr. 1982, 257-261.

The compounds wherein Y=$Y^1$=hydroxyl may be prepared by dehydrogenation of the corresponding cyclohexane-1,3 diones by the method described by E. D. Berymann, et al., JACS, 1953, 3226. Compounds of formula I' wherein both of Z is N, Y is oxo and $Y^1$ is hydroxyl may be prepared as described in WO 2005/007632 and J. Het. Chem. 1989, 169-176.

In all of the above formulae, as well as in those provided hereinafter, the straight lines represent bonds. Where there is no symbol for the atoms between the bonds, the appropriate carbon-containing radical is to be inferred.

Pharmaceutical compositions may be prepared by combining a therapeutically effective amount of at least one compound according to the present invention, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five unit doses, where a typical unit dose is from one to about 8 drops, preferably one to about 3 drops. The volume of one drop usually is about 20-35 µl.

The compounds disclosed herein for use in the method of this invention, i.e. the treatment of glaucoma or elevated intraocular pressure, may also be used in combination with other drugs useful for the treatment of glaucoma or elevated intraocular pressure.

For the treatment of glaucoma or elevated intraocular pressure, combination treatment with the following classes of drugs are contemplated:

β-Blockers (or β-adrenergic antagonists) including carteolol, levobunolol, metipranolol, timolol hemihydrate, timolol maleate, β1-selective antagonists such as betaxolol, and the like, or pharmaceutically acceptable salts or prodrugs thereof;

Adrenergic Agonists including
non-selective adrenergic agonists such as epinephrine borate, epinephrine hydrochloride, and dipivefrin, and the like, or pharmaceutically acceptable salts or prodrugs thereof; and
$\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including
direct acting cholinergic agonists such as carbachol, pilocarpine hydrochloride, pilocarpine nitrate, pilocarpine, and the like, or pharmaceutically acceptable salts or prodrugs thereof;
cholinesterase inhibitors such as demecarium, echothiophate, physostigmine, and the like, or pharmaceutically acceptable salts or prodrugs thereof;

Glutamate Antagonists such as memantine, amantadine, rimantadine, nitroglycerin, dextrophan, dextromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedipine, nimodipine, barnidipine, lidoflazine, prenylamine lactate, amiloride, and the like, or pharmaceutically acceptable salts or prodrugs thereof;

Prostamides such as bimatoprost, or pharmaceutically acceptable salts or prodrugs thereof; and Prostaglandins including travoprost, UFO-21, chlorprostenol, fluprostenol, 13,14-dihydro-chloprostenol, isopropyl unoprostone, latanoprost and the like.

The invention is further illustrated by the following non-limiting Examples.

Example 1

Intraocular Pressure

Intraocular pressure was measured by applanation pneumatonometry in conscious animals. The test compound was administered topically to one eye while vehicle was given to the fellow eye in a masked fashion. Ocular normotensive Beagle dogs (males, females) were dosed once daily for five days. Laser-induced unilaterally ocular hypertensive Cynomolgus monkeys (females) were dosed once daily for 4 days.

Student's paired t-test was used for statistical comparisons. Differences were considered statistically significant if the P-value is less than 0.05.

The results are shown in the Figures.

The figures show the change from baseline IOP of Monkey dosed with 0.1% of the active compound versus time.

Example 2

Determination of Abnormal Cannabidiol Activity

Abnormal Cannabidiol receptor activity may be measured in accordance with the procedure disclosed in (Wagner J A et al., *Hypertension* 33 [part II], 429 (1999); Járai Z et al., *PNAS* 96, 14136 (1999), which is hereby incorporated by reference in its entirety.

Experimental Details for Synthesis of Abnormal Cannabidiols

General Route

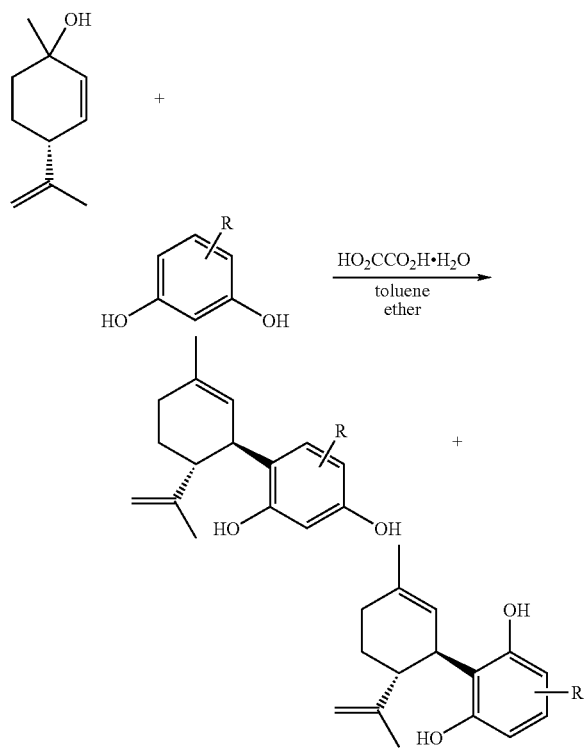

Example 3

5-methyl-4-(6-Isoprenyl-3-methylcyclohex-2-enyl) benzene-1,3-diol (4R)-1-Methyl-4-isoprenylcyclohex-2-ene-1-ol (300 mg, 2 mmoles) was dissolved in toluene (20 ml) and 5-methylresorcinol (248 mg, 2 mmoles) was added in diethyl ether (5 ml). Oxalic acid dihydrate (252 mg, 2 mmoles) was added and the reaction mixture heated with stirring at 80° for 5 hours. The reaction mixture was allowed to cool and diluted with diethyl ether (30 ml). The ether solution was washed twice with aqueous sodium bicarbonate and dried over anhydrous magnesium sulphate. The solvents were evaporated under reduced pressure to give the crude product as a brown oil (800 mg). The product was purified using a silica column eluted with ethyl acetate:isohexane 1:9 going to ethyl acetate:isohexane 2:8.

The product was isolated as a yellow gum (106 mg)

Example 4

4-(6-Isoprenyl-3-methylcyclohex-2-enyl)benzene-1, 3-diol

The named compound is prepared according to the method described in Example 3 except that resorcinol is substituted for 5-methylresorcinol.

$^1$H NMR (300 MHz, CDCl$_3$) 6.2 (M, 2H), 6.1 (S, 1H), 5.55 (M, 1H), 4.7 (M, H), 4.55 (S, 1H), 4.5 (M, 1H), 3.55 (M, 1H), 2.5 (M, 1H), 2.2 (M, 2H), 2.15 (S,3H), 1.85 (M,2H), 1.8 (S,3H), 1.6 (S,3H)

Also prepared in a similar manner were

Example 5

5-Chloro-4-(6-Isoprenyl-3-methylcyclohex-2-enyl) benzene-1,3-diol $^1$H NMR (300 MHz, CDCl$_3$) 6.4 (M, 1H), 6.3 (M, 1H), 6.25 (S, 1H), 5.6 (M, 1H), 4.7 (brS, 1H), 4.65 (M, 1H), 4.4 (M, 1H), 4.0 (M, 1H), 2.5 (M, 1H), 2.25 (M, 1H), 2.15 (M, 1H), 1.85 (M, 2H), 1.8 (S, 3H), 1.6 (S, 3H)

Example 6

4-(6-Isoprenyl-3-methylcyclohex-2-enyl)-5-methoxybenzene-1,3-diol $^1$H NMR (300 MHz, CDCl$_3$) 6.15 (brS, 1H), 6.0 (M, 2H), 5.6 (M, 1H), 4.65 (brS, 1H), 4.5 (M, 1H), 4.35 (M, 1H), 3.95 (M, 1H), 3.7 (S,3H), 2.4 (M, 1H), 2.25 (1H, M), 2.1 (M, 1H), 1.8 (M, 2H), 1.8 (S, 3H), 1.65 (S, 3H)

Example 7

2-(6-Isoprenyl-3-methylcyclohex-2-enyl)-5-methoxybenzene-1,3-diol $^1$H NMR (300 MHz, CDCl$_3$) 6.0 (brS, 2H), 5.55 (M, 1H), 4.7 (M, 1H), 4.6 (M, 1H), 3.8 (M, 1H), 3.75 (S, 3H), 2.4 (M, 1H), 2.2 (M, 1H), 2.1 (M, 1H), 1.8 (S, 3H), 1.8 (M, 2H)

Example 8

Synthesis of 6-Chloro-4-(6-Isoprenyl-3-methylcyclohex-2-enyl)benzene-1,3-diol

4-Chlororesorcinol (350 mg, 2.4 mmoles) was dissolved in toluene (30 ml) and diethyl ether (20 ml) and p-toluenesulphonic acid (91 mg, 0.48 mmoles) was added.

(4R)-1-Methyl-4-isoprenylcyclohex-2-ene-1-ol (500 mg, 3 mmoles) in toluene (10 ml) was added and the reaction mixture was stirred at room temperature for 6 hours. Diluted with diethyl ether (30 ml) and washed twice with aqueous sodium bicarbonate. Dried over anhydrous magnesium sulphate and the solvent was evaporated under reduced pressure to give a yellow gum (800 mg). Purified using a silica column eluted with ethyl acetate:isohexane 9:1 going to ethyl acetate: isohexane 8:2. The product was isolated as a yellow gum (95 mg).

¹H NMR (300 MHz, CDCl₃) 6.9 (S, 1H), 6.5 (S, 1H), 5.5 (S, 1H), 5.45 (M, 1H), 5.35 (S, 1H), 4.7 (M, 1H), 4.6 (M, 1H), 3.35 (M, 1H), 2.2 (M, 3H), 1.8 (M,3H), 1.75 (M,2H), 1.6 (S,3H)

Example 9

Synthesis of 4-Cyclohexylbenzene-1,3-diol

This compound was prepared as described in JACS, 1953, 2341.

Resorcinol (2.2 g, 0.02 moles) was mixed with cyclohexanol (1 g, 0.01 moles) and zinc (II) chloride (0.48 g, 0.0035 moles) and the reaction mixture heated to 150° with stirring. After heating 2 hours, the reaction mixture was allowed to cool and then dissolved in ethyl acetate. Washed with water and dried over anhydrous magnesium sulphate. The solvent was evaporated to give a brown oil (3.0 g). Excess resorcinol was evaporated by heating in a Kugelrohr oven under reduced pressure (200°, 2 mmHg). Purified using a silica column eluted with ethyl acetate:isohexane 2:8 to give the product as a yellow oil (0.5 g). Trituration with isohexane gave the product as a white solid (0.2 g).

¹H NMR (300 MHz, CDCl₃) 7.0 (D, 1H J=8 Hz), 6.4 (M, 1H), 6.3 (M, 1H), 4.7 (S, 1H), 4.55 (S, 1H), 2.7 (M, 1H), 1.8 (M,5H), 1.4 (M,5H)

Example 10

Synthesis of 4R-Isoprenyl-1-methylcyclohex-2-enol

The synthesis of 4R-Isoprenyl-1-methylcyclohex-2-enol was carried out as described in WO2004096740.

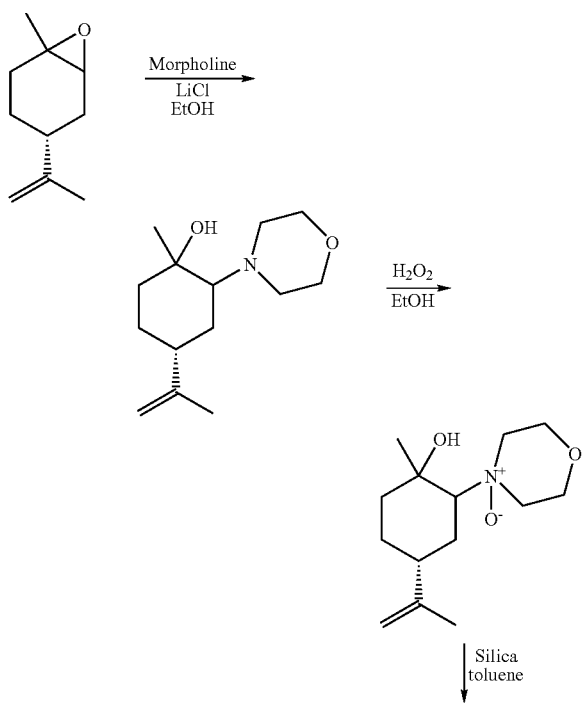

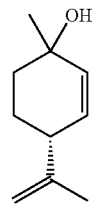

Example 11

4-Isoprenyl-1-methyl-2-morpholin-4-yl-cyclohexanol (+)-Limonene oxide (13.2 g, 0.087 moles) was dissolved in ethanol (40 ml) and lithium chloride (5.9 g, 0.14 moles) was added with stirring. Morpholine (11.4 g, 0.13 moles) was added and the reaction mixture was heated at 60° for 48 hours. The solvent was evaporated under reduced pressure and the residue taken up in dichloromethane. Washed with water. Extracted into 2M hydrochloric acid and washed with dichloromethane. Basified to pH 10 by addition of 2M sodium hydroxide. Extracted with diethyl ether and washed with water. Dried over anhydrous magnesium sulphate and evaporated the solvent under reduced pressure to give the product as a yellow oil (10.3 g).

¹H NMR (300 MHz, CDCl₃) 4.95 (M, 1H), 4.85 (M, 1H), 3.7 (M, 4H), 2.75 (M, 2H), 2.5 (M, 4H), 2.1 (M, 1H), 1.95 (M, 1H), 1.75 (S, 3H), 1.6 (M, 4H), 1.2 (S, 3H)

Example 12

4-Isoprenyl-1-methyl-2-(4-oxy-morpholin-4-yl)-cyclohexanol

4-Isoprenyl-1-methyl-2-morpholin-4-yl-cyclohexanol (17.7 g, 0.074 moles) was dissolved in ethanol (100 ml) and 35% hydrogen peroxide (37 ml, 0.325 moles) was added. Heated with stirring at 50° for 6 hours. 5% palladium on carbon (100 mg) was added in order to decompose the excess peroxide. Stirred at room temperature for 3 hours. (Peroxide test papers gave a negative result.)

Filtered through a pad of HiFlo to remove the palladium on carbon and the solvent was evaporated under reduced pressure to give the product as a yellow oil (22.2 g).

¹H NMR (300 MHz, CDCl₃) 5.5 (M, 1H), 4.85 (M, 1H), 4.5 (M, 2H), 3.7 (M, 4H), 3.4 (M, 3H), 2.95 (M, 1H), 2.65 (M, 1H), 2.25 (M, 1H), 2.0 (M, 1H), 1.85 (M, 1H), 1.75 (M, 1H), 1.75 (S, 3H), 1.55 (M, 1H), 1.55 (S, 3H)

Example 13

4R-Isoprenyl-1-methylcyclohex-2-enol

4-Isoprenyl-1-methyl-2-morpholin-4-yl-cyclohexanol (4.6 g, 0.018 moles) was dissolved in toluene (80 ml) and silica (1.1 g) was added. The reaction mixture was heated to reflux with stirring. Water generated in the reaction was removed using Dean and Stark apparatus. After refluxing overnight, the silica was removed by filtration and the filtrate evaporated under reduced pressure to give a brown oil (4.0 g). Dissolved in dichloromethane and washed with 2M hydrochloric acid. Washed with water and dried over anhydrous magnesium sulphate. The solvent was removed by evaporation under reduced pressure to give the product as a brown oil (1.3 g).

¹H NMR (300 MHz, CDCl₃) 5.7 (M, 2H), 4.8 (M, 2H), 2.7 (M, 1H), 1.8 (M,2H), 1.75 (S,3H), 1.65 (M,2H), 1.3 (S,3H)

Experimental details for Synthesis of Tetrahydropyridines

Scheme 1

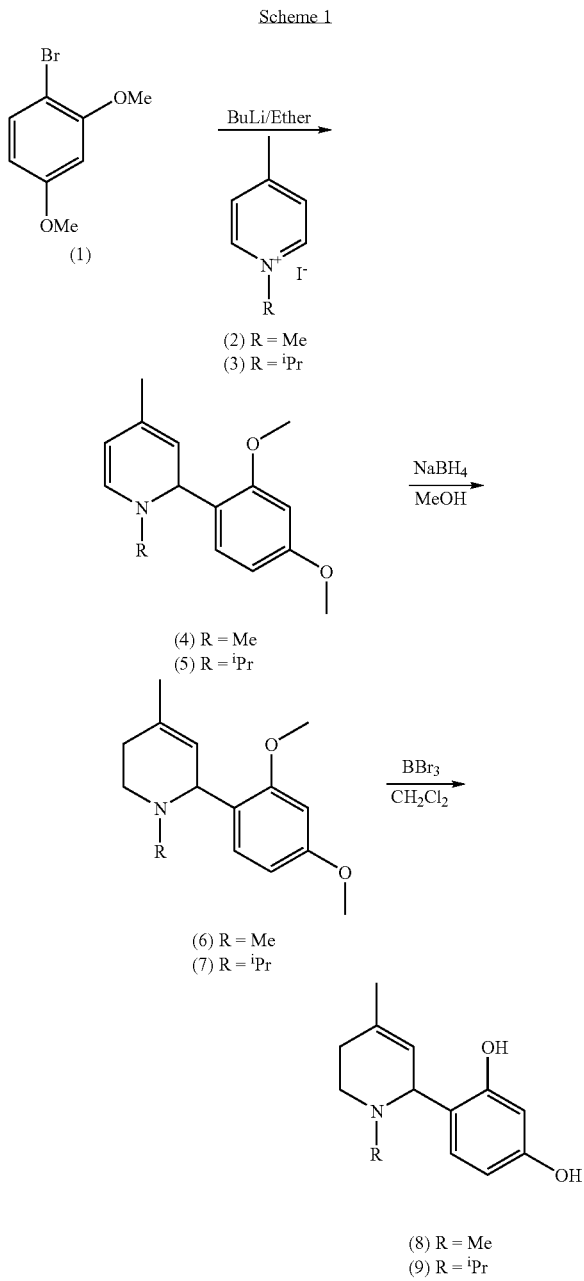

Example 14

Preparation of 2-(2,4-Dimethoxyphenyl)-1,4-dimethyl-1,2-dihydropyridine

To a stirred solution of 2,4-dimethoxybromobenzene (1) (0.5 g, 2.3 mmol) in diethyl ether (10 ml) cooled at −78° C. under nitrogen was added a solution of n-butyl lithium (1.0 ml, 2.5 mmol of 2.5M solution in hexane) drop wise. The mixture was stirred at −78° C. for 2 hours and then 1,4-dimethyl pyridinium iodide (2) (0.54 g, 2.5 mmol) was added as a solid. The resultant mixture was allowed to warm to room temperature and stirred at room temperature for 18 hours. The mixture was diluted with water (20 ml) and extracted with diethyl ether (2×15 ml). The combined organic extracts were dried over anhydrous magnesium sulphate, filtered and evaporated to yield 2-(2,4-dimethoxyphenyl)-1,4-dimethyl-1,2-dihydropyridine (4) (0.5 g, 93%) as a brown oil, ¹H NMR CDCl₃??1.7 (s, 3H), 2.7 (s, 3H), 3.8 (s, 6H), 4.45 (dd, 1H, J=2.7) 4.85 (m, 1H), 5.4 (d, 1H, J=4), 6.05 (d, 1H, J=7), 6.45 (d, 1H, J=3), 6.55 (m, 1H), 7.5 (d, 1H, J=9).

By proceeding in a similar manner starting from 2,4-dimethoxybromobenzene (1) and 1-isopropyl-4-methyl pyridinium iodide (3), 2-(2,4-dimethoxyphenyl)-1-isopropyl-4-methyl-1,2-dihydropyidine (5) was prepared, ¹H NMR CDCl₃? (d, 6H J=7), 1.7 (s, 3H), 3.15 (m, 1H), 3.7 (s, 6H), 4.5 (d, 1H J=8), 4.8 (m,1H), 5.5 (5, 1H J=5), 6.3 (d, 1H J=7), 6.45 (d, 1H J=2), 6.55 (m, 1H), 7.55 (d, 1H J=8).

Example 15

Preparation of 6-(2,4-Dimethoxyphenyl)-1,4-dimethyl-1,2,3,6-tetrahydro-pyridine (6)

To a stirred solution of 2-(2,4-dimethoxyphenyl)-1,4-dimethyl-1,2-dihydropyridine(4) (0.48 g, 2.06 mmol) in methanol (5 ml) at room temperature was added sodium borohydride (98 mg, 2.51 mmol), gas evolution commenced immediately, the resulting mixture was stirred for 3 hours. At this time the solvent was evaporated and the residue suspended in water (5 ml) and extracted with ethyl acetate (2×10 ml). The organic extract was then extracted with 2M hydrochloric acid (2×15 ml). The aqueous layer was basified with 2M sodium hydroxide and extracted with ethyl acetate (2×20 ml), the organic extract was dried over anhydrous magnesium sulphate, filtered and evaporated to yield 6-(2,4-dimethoxyphenyl)-1,4-dimethyl-1,2,3,6-tetrahydropyridine (6) (350 mg, 73%) as a yellow oil, ¹H NMR CDCl₃ δ?1.55 (s, 3H), 1.9 (m, 1H), 2.2 (s, 3H), 2.5 (m, 2H), 2.95 (m, 1H), 3.8 (s, 6H), 4.1 (m, 1H), 5.2 (m, 1H), 6.5 (m, 2H), 7.3 (d, 1H J=4).

By proceeding in a similar manner starting from 2-(2,4-dimethoxyphenyl)-1-isopropyl-4-methyl-1,2-dihydropyridine (5), 6-(2,4-dimethoxyphenyl)-1-isopropyl-4-methyl-1,2,3,6-tetrahydropyridine (7) was prepared, ¹H NMR CDCl₃ δ 0.95 (d, 3H J=6), 1.05 (d, 3H J=6), 1.7 (s, 3H), 1.9 (m, 1H), 2.5 (m, 1H), 2.85 (m, 1H), 3.0 (m,1H), 3.8 (s, 6H), 4.6 (s, 1H), 5.2 (s, 1H), 6.45 (d, 1H J=3), 6.5 (dd, 1H J=3.8), 7.4 (d, 1H J=8).

Example 16

Preparation 4-(1,4-Dimethyl-1,2,5,6-tetrahydropyridin-2-yl)-benzene-1,3-diol (8)

To a stirred solution of 6-(2,4-dimethoxyphenyl)-1,4-dimethyl-1,2,3,6-tetrahydro-pyridine (6) (300 mg, 1.27 mmol) in dichloromethane (20 ml) cooled at 0° C. under nitrogen was added boron tribromide (3.1 ml, 3.18 mmol of 1.0M solution in dichloromethane), the resultant dark solution was allowed to warm to room temperature and stirred for 1 hour. The solution was poured onto ice and basified with sodium bicarbonate. The layers were separated and the aqueous layer was extracted with dichloromethane (20 ml), the combined organic layers were dried over anhydrous magnesium sulphate, filtered and evaporated to a gum (200 mg). The material was purified on a 10 g silica cartridge eluting with methanol/dichloromethane/ammonia (7:92:1) to yield 4-(1,4-dimethyl-1,2,5,6-tetrahydropyridin-2-yl)-benzene-1,3-diol (8) (93 mg, 35%) as a gum, ¹H NMR D6-acetone ??1.67 (s, 3H), 1.97 (m,1H), 2.3 (s, 3H), 2.42 (m, 1H), 2.74 (m, 1H), 3.08 (m, 1H), 3.74 (s, 1H), 5.15 (s, 1H), 6.2 (d, 1H J=2), 6.27 (dd, 1H J=2.8), 6.82 (d, 1H J=8), 9.4 (bs, 2H).

By proceeding in a similar manner starting from 6-(2,4-dimethoxyphenyl)-1-isopropyl-4-methyl-1,2,3,6-tetrahydropyridine (7), 4-(1-isopropyl-4-methyl-1,2,5,6-tetra-hydropyridin-2-yl)-benzene-1,3-diol (9) was prepared, NMR D6-acetone δ 0.81 (d, 3H J=7), 0.98 (d, 3H J=7), 1.52 (s, 3H), 1.84 (m, 1H), 2.15 (m, 1H), 2.29 (m, 1H), 2.94 (m, 2H), 4.09 (s, 1H), 4.97 (s, 1H), 6.05 (d, 1H J=3), 6.11 (dd, J=3.8), 6.68 (d, J=8), 9.6 (bs, 2H).

Example 17

Preparation of 1-Isopropyl-4-methyl pyridinium iodide (3)

To a stirred solution of 4-picoline (2.5 g, 26.8 mmol) in acetonitrile (50 ml) was added isopropyl iodide (9.1 g, 53.6 mmol) drop wise, the resultant mixture was heated at 90° C. for 24 hours. After cooling the solvent was evaporated to give a red solid which on trituration with ethyl acetate yielded 1-isopropyl-4-methyl pyridinium iodide (6.01 g, 85%) as a cream solid, $^1$H NMR D6-DMSO δ?1.6 (d, 6H, J=7), 2.6 (s, 3H), 4.95 (m, 1H), 8.0 (d, 2H J=6), 9.05 (d, 2H J=6).

Preparation of 1-Aryl-piperidine2,4-diones

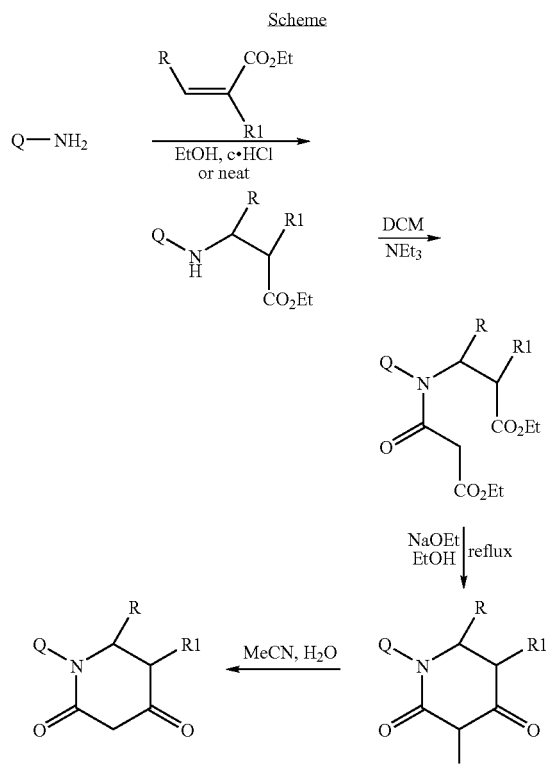

Scheme

Example 18

Preparation of Ethyl 3-(3-Chlorophenylamino)propionate

3-Chloroaniline (3.8 g, 0.03 moles) was dissolved in ethanol (5 ml) and ethyl acrylate (3.3 g, 0.033 moles) was added in ethanol (5 ml). Concentrated hydrochloric acid (1 ml) was added and the reaction mixture was heated at reflux for 48 hours. Evaporated to a low bulk and dissolved the residue in dichloromethane and water. Basified to pH 9 with aqueous ammonia and separated. Evaporated off the dichloromethane under reduced pressure to give the crude product as a yellow oil (5.4 g) Purified using a silica column eluted with isohexane:ethyl acetate 9:1 to give the required product (3.5 g, 51%) as a colourless oil.

$^1$H NMR CDCl$_3$ δ 1.30 (t, 3H, J=6.5 Hz), 2.65 (t, 2H, J=6 Hz), 3.45 (q, 2H J=6 Hz), 4.20 (q, 2H, J=6.5 Hz), 6.50 (m, 1H), 6.60 (m, 1H), 6.70 (m, 1H), 7.10 (m, 1H)

Example 19

Preparation of N-(3-Chlorophenyl)-N-(2-ethoxycarbonyl-ethyl)-malonamic acid ethyl ester Ethyl 3-(3-Chlorophenylamino)propionate (3.5 g, 0.0154 moles) was dissolved in dichloromethane (40 ml) and ethyl malonyl chloride (2.55 g, 0.017 moles) was added dropwise in dichloromethane (10 ml) with stirring and cooling in order to keep the reaction temperature below 20°. Triethylamine (1.72 g, 0.017 moles) was added dropwise in dichloromethane (10 ml). The reaction temperature was kept below 20° by ice bath cooling. The reaction mixture was allowed to warm to room temperature and stirred at room temperature overnight. Washed with 2M hydrochloric acid, water and sodium bicarbonate solution. Dried over anhydrous magnesium sulphate, filtered and evaporated to give the required product as an orange oil. (4.5 g, 86%)

$^1$H NMR CDCl$_3$ δ 1.25 (m, 6H), 2.65 (t, 2H, J=7 Hz), 3.20 (s, 2H), 4.10 (m, 4H), 7.15 (m, 1H), 7.30 (m, 1H), 7.40 (m, 2H)

Example 20

Preparation of Ethyl 1-(3-chlorophenyl)piperidine-2,4-dione carboxylate

Sodium (0.7 g, 0.029 moles) was dissolved in ethanol (90 ml) and N-(3-Chlorophenyl)-N-(2-ethoxycarbonyl-ethyl)-malonamic acid ethyl ester (4.5 g, 0.0132 moles) was added in ethanol (30 ml). The reaction mixture was heated at reflux overnight. The ethanol was evaporated off and the residue dissolved in water. Washed with diethyl ether and acidified to pH2 with concentrated sulphuric acid. Extracted with dichloromethane and the combined dichloromethane extracts were combined. Washed with water and dried over anhydrous magnesium sulphate. Filtered and evaporated to give the product as an orange oil (2.8 g, 72%).

$^1$H NMR CDCl$_3$ δ 1.40 (t, 3H, J=5 Hz), 2.85 (t, 2H, J=6 Hz), 3.85 (t, 2H J=6 Hz), 4.40 (q, 2H, J=5 Hz), 7.20 (m, 2H), 7.30 (m, 1H), 7.35 (m, 1H)

Example 21

Preparation of 1-(3-Chlorophenyl)piperidine-2,4-dione

Ethyl 1-(3-chlorophenyl)piperidine-2,4-dione carboxylate (2.8 g, 0.0095 moles) was dissolved in acetonitrile (100 ml)/water (10 ml) and refluxed for 2 hours. Evaporated to a low bulk and dissolved in dichloromethane. Washed with water and dried over anhydrous magnesium sulphate. Filtered and evaporated to give the product as an orange oil (2.2 g). Purified using a silica column eluted with dichloromethane:ethyl acetate 9:1 to give the required product as a pale yellow gum (1.2 g, 59%).

$^1$H NMR CDCl$_3$ δ 2.80 (t, 2H, J=6 Hz), 3.55 (s, 2H), 4.05 (t, 2H, J=6 Hz), 7.20 (m, 1H), 7.30 (m, 1H), 7.35 (m, 1H), 7.40 (m, 1H)

Also prepared in a similar manner were

1-Phenylpiperidine-2,4-dione $^1$H NMR CDCl$_3$, ppm) δ 2.80 (t, 2H, J=6 Hz), 3.6 (s, 2H), 4.05 (t, 2H, J=6 Hz), 7.30 (m, 3H), 7.45 (m, 2H)

1-(3-Methylphenyl)piperidine-2,4-dione $^1$H NMR (CDCl$_3$, ppm) δ 2.40 (s, 3H), 2.80 (t, 2H, J=6.5 Hz), 3.6 (s, 2H), 4.05 (t, 2H, J=6.5 Hz), 7.30 (m, 3H), 7.45 (m, 2H)

1-(4-Fluorophenyl)piperidine-2,4-dione $^1$H NMR CDCl$_3$, ppm) δ 2.80 (t, 2H, J=6 Hz), 3.55 (s, 2H), 4.0 (t, 2H, J=6 Hz), 7.1 (m, 2H), 7.25 (m, 2H)

1-(3,5-Difluorophenyl)piperidine-2,4-dione $^1$H NMR (CDCl$_3$, ppm) δ 2.80 (t, 2H, J=6 Hz), 3.58 (s, 2H), 4.04 (t, 2H, J=6 Hz), 6.68-6.83 (m, 1H), 6.84-6.99 (m, 2H).

1-(3,5-Dichlorophenyl)piperidine-2,4-dione $^1$H NMR (CDCl$_3$, ppm) δ 2.80 (t, 2H, J=6 Hz), 3.58 (s, 2H), 4.02 (t, 2H, J=6 Hz), 7.20-7.36 (m, 3H).

1-(4-Methylpyrid-2-yl)piperidine-2,4-dione $^1$H NMR (CDCl$_3$, ppm) δ 2.41 (s, 3H), 2.75 (t, 2H, J=6 Hz), 3.62 (s, 2H), 4.44 (t, 2H, J=6 Hz), 6.94-7.02 (m, 1H), 7.72-7.79 (m, 1H), 8.25-8.36 (m, 1H).

Preparation of Cyclohexane-1,3-diones

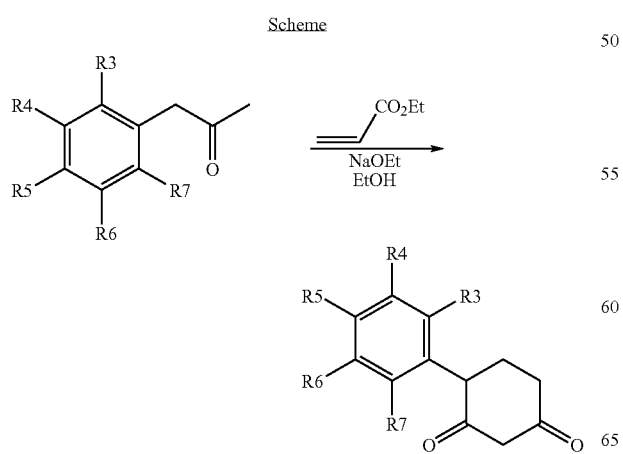

Example 22

Preparation of 4-(4-Fluorophenyl)cyclohexane-1,3-dione

Sodium (0.3 g, 0.013 moles) was dissolved in ethanol (50 ml) and 4-Fluorophenylacetone (2.0 g, 0.013 moles) was added in ethanol (10 ml). Ethyl acrylate (1.3 g, 0.013 moles) was and the reaction mixture was heated at reflux overnight. The reaction mixture was allowed to cool and evaporated under reduced pressure to give a brown gum. Dissolved in water and washed with diethyl ether. The aqueous layer was acidified to pH2 with conc. Hydrochloric acid and extracted with dichloromethane. The extracts were combined and washed with water. Dried over anhydrous magnesium sulphate and filtered. The filtrate was evaporated to give an orange oil. (1.7 g) This was purified using a silica column eluted with dichloromethane:ethyl acetate 8:2 and then dichloromethane:ethyl acetate 2:1 to give a colorless gum. (0.428 g) This was triturated with diethyl ether/isohexane to give 4-(4-Fluorophenyl)cyclohexane-1,3-dione (0.28 g) as a white solid.

$^1$H NMR (CD$_3$OD, ppm) δ 2.1 (m, 1H), 2.3 (m, 1H), 2.4 (m, 2H), 3.7 (m, 1H), 4.9 (s, 2H), 7.1 (m, 2H), 7.2 (m, 2H).

Also prepared in a similar manner

4-Phenylcyclohexane-1,3-dione $^1$H NMR (CD$_3$OD, ppm) δ 2.15 (m, 1H), 2.3 (m, 3H), 3.7 (m, 1H), 4.9 (s, 2H), 7.2 (m, 3H), 7.3 (m, 2H).

Preparation of Pyridazin-3-ones

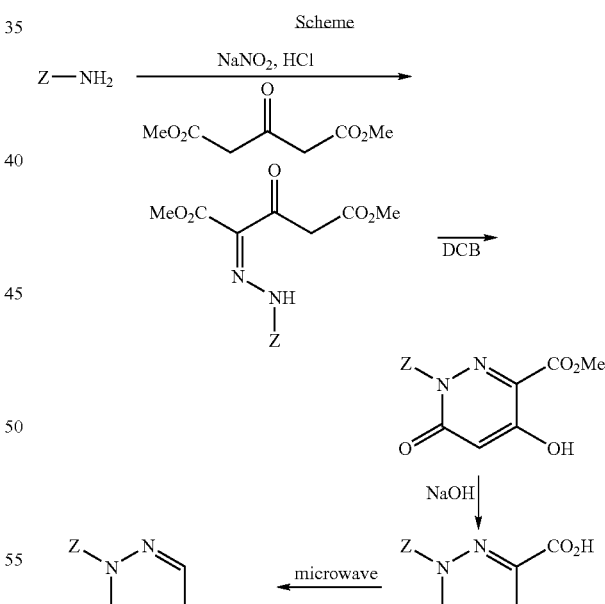

Example 23

3-Oxo-2-phenylhydrazono)pentanedioic acid dimethylester

To a mixture of aniline (1.86 g, 20 mmol) in concentrated hydrochloric acid (10 ml) and water (20 ml) at a temperature below 5° C. was added a solution of sodium nitrite (1.38 g, 20 mmol) in water (15 ml) drop wise. The resultant mixture was stirred for 15 minutes and then it was poured into a solution of dimethylacetonedicarboxylate (3.48 g, 20 mmol) and sodium acetate (12 g, 0.146 mol) in ethanol (12 ml) and water (40 ml) causing an immediate precipitation. The suspension was stirred for 1 hour and then extracted with ethyl acetate (3×125 ml). The combined organic extracts were dried over anhydrous magnesium sulphate, filtered and evaporated to yield 3-oxo-2-phenylhydrazono)pentanedioic acid dimethyl ester as a red oil (5.58 g, quantitative) consisting of a mixture of E and Z isomers about the hydrazone.

$^1$NMR CDCl$_3$ δ☐☐☐ (singlets, 8H), 7.1-7.5 (m, 5H), 12.8 (s, 1H).

Example 24

Methyl 4-hydroxy-6-oxo-1-phenyl-1,6-dihydropyridazine-3-carboxylate

3-Oxo-2-phenylhydrazono)pentanedioic acid dimethyl ester (12.5 mmol) was dissolved in dichlorobenzene and heated at reflux for 24 hours and then allowed to cool to room temperature. The solvent was evaporated and the residue triturated with ether to give methyl 4-hydroxy-6-oxo-1-phenyl-1,6-dihydropyridazine-3-carboxylate a beige solid (2.4 g, 78%).

1H NMR CDCl$_3$ δ 4.0 (s, 3H), 6.4 (s, 1H), 7.4-7.6 (m, 5H), 10.3 (s, 1H).

Example 25

4-Hydroxy-6-oxo-1-phenyl-1,6-dihydropyridazine-3-carboxylic acid

Methyl 4-hydroxy-6-oxo-1-phenyl-1,6-dihydropyridazine-3-carboxylate (0.8 g, 3.24 mmol) was suspended in sodium hydroxide solution (20 ml of 2.0M) and heated at reflux for 1 hour. The mixture was allowed to cool to room temperature, acidified with 2M hydrochloric acid and extracted with ethyl acetate (3×15 ml). The combined organic extracts were dried over anhydrous magnesium sulphate, filtered and evaporated to yield 4-hydroxy-6-oxo-1-phenyl-1,6-dihydropyridazine-3-carboxylic acid as a yellow solid (0.6 g, 80%).

$^1$H NMR CDCl$_3$ δ 6.3 (s, 1H), 7.35-7.7 (m, 5H).

Example 26

5-Hydroxy-2-phenyl-2H-pyridazin-3-one

4-Hydroxy-6-oxo-1-phenyl-1,6-dihydropyridazine-3-carboxylic acid (400 mg, 1.72 mmol) was heated at 270° C. in a microwave for 3 minutes. The resultant black mixture was extracted into saturated sodium bicarbonate (15 ml). The sodium bicarbonate solution was acidified with concentrated hydrochloric acid and extracted with ethyl acetate (3×15 ml). The combined organic extracts were dried over anhydrous magnesium sulphate, filtered and evaporated to a crude solid (300 mg). This was purified on a 10 g SPE cartridge eluting with dichloromethane/ethyl acetate (80:20 to 60:40) to yield 5-hydroxy-2-phenyl-2H-pyridazin-3-one (60 mg) as a beige solid.

$^1$H NMR D6 DMSO δ 6.05 (d, 1H, J=2.7 Hz), 7.4-7.6 (m, 5H), 7.85 (d, 1H, J=2.7 Hz), 11.6 (s, 1H).

The following compounds are also active in the method of the present invention:

2-(4-Chlorophenyl)-5-hydroxy-2H-pyridazin-3-one

5-Hydroxy-2-(3-trifluoromethylphenyl)-2H-pyridazin-3-one

The following synthesis is described in J. Het. Chem. 1989, 26, 169-176

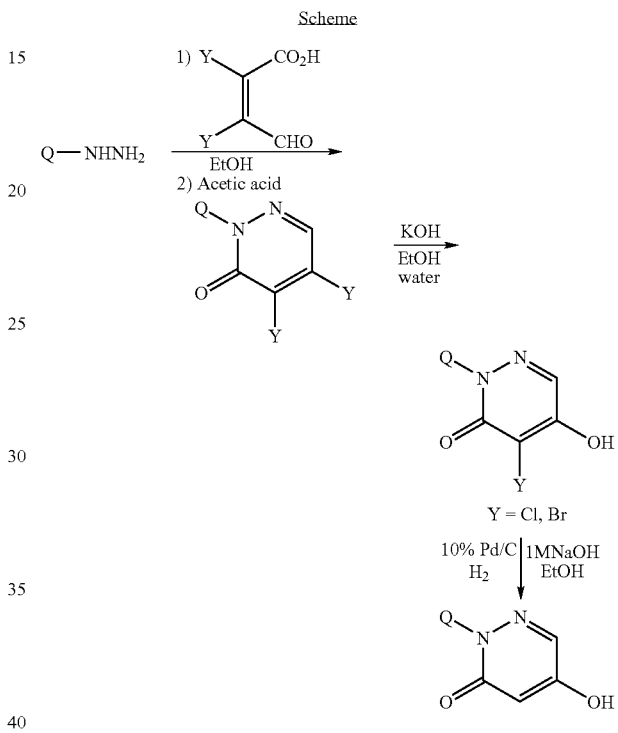

Scheme

Example 27

2-(3,5-Difluorophenyl)-5-hydroxypyridazin-3-one

4-Bromo-2-(3,5-difluorophenyl)-5-hydroxypyridazin-3-one (0.6 g, 1.98 mmoles) was dissolved in ethanol (50 ml) and 1M sodium hydroxide (4 ml) was added. 10% Palladium on carbon (0.15 g) was added and the flask was placed under an atmosphere of hydrogen (balloon) with stirring. The reaction mixture was stirred overnight at room temperature. Filtered off the catalyst using Hyflo and evaporated to dryness. Added 2M hydrochloric acid and extracted into ethyl acetate. Washed with water and dried over anhydrous magnesium sulphate. Filtered and evaporated the filtrate to give a white solid. Triturated with diethyl ether to give the product as a white solid. (0.32 g, 72%)

1H NMR DMSOd6 δ 12.2 (br s, 1H), 7.9 (d, 1H, J=3 Hz), 7.3 (m, 5H), 6.1 (d, 1H, J=3 Hz)

Also prepared in a similar manner 2-(2,5-Difluorophenyl)-5-hydroxypyridazin-3-one $^1$H NMR DMSOd6 δ 11.8 (br s, 1H), 7.85 (d, 1H, J=2.5 Hz), 7.4 (m, 4H), 6.1 (d, 1H, J=2.5 Hz)

Example 28

4-Bromo-2-(3,5-difluorophenyl)-5-hydroxypyridazin-3-one 4,5-Dibromo-2-(3,5-difluorophenyl)pyridazin-3-one (1.5 g, 0.0041 moles) was suspended in ethanol (50 ml) and potassium hydroxide (0.8 g, 0.0123 moles) was added in water (8 ml). Refluxed for 4 hours with stirring. Evaporated to a low bulk and diluted with water. Acidified to pH2 with conc. hydrochloric acid and extracted with ethyl acetate. Washed with water and dried with anhydrous magnesium sulphate. Filtered and evaporated the filtrate to give an orange solid. Triturated with diethyl ether and dried in a desiccator to give the product as a cream solid. (0.7 g, 56%)

$^1$H NMR DMSOd6 δ 12.5 (br s, 1H), 7.9 (s, 1H), 7.35 (m, 3H); $^{19}$F NMR δ 110

Also prepared in a similar manner

4-Bromo-2-(2,5-difluorophenyl)-5-hydroxypyridazin-3-one $^1$H NMR DMSOd6 δ 7.9 (s, 1H), 7.5 (m, 3H); $^{19}$F NMR δ 117, 126

4-Bromo-2-(2,5-dichlorophenyl)-5-hydroxypyridazin-3-one $^1$H NMR DMSOd6 δ 7.9 (s, 1H), 7.8 (d, 1H, J=2.5 Hz), 7.7 (d, 1H, J=8.5 Hz), 7.6 (d,d, 1H, J=2.5, 8.5 Hz)

Example 29

4,5-Dibromo-2-(3,5-difluorophenyl)pyridazin-3-one

Mucobromic acid (2.8 g, 0.011 moles) was dissolved in ethanol (75 ml) and 3,5-difluorophenyl hydrazine hydrochloride (1.8 g, 0.01 moles) was added. After 30 minutes, triethylamine (1.4 ml, 0.01 moles) was added. The reaction mixture was stirred at room temperature for 3 hours. Evaporated to a low bulk and the residue was suspended in glacial acetic acid (80 ml). Refluxed with stirring overnight to give a brown solution. Evaporated to dryness and triturated with methanol to give the required product as a pale brown solid. (3.4 g, 93%)

$^1$H NMR DMSOd6 δ 8.3 (s, 1H), 7.4 (m, 3H); $^{19}$F NMR δ 109

Also prepared in a similar manner

4,5-Dibromo-2-(2,5-dichlorophenyl)pyridazin-3-one $^1$H NMR DMSOd6 δ 7.9 (s, 1H), 7.45 (m, 1H), 7.4 (m, 2H)

4,5-Dibromo-2-(3,5-dichlorophenyl)pyridazin-3-one $^1$H NMR DMSOd6 δ 8.35 (s, 1H), 7.8 (m, 1H), 7.7 (m,2H)

4,5-Dibromo-2-(2,5-difluorophenyl)pyridazin-3-one $^1$H NMR DMSOd6 δ 8.35 (s, 1H), 7.5 (m, 3H)

Scheme

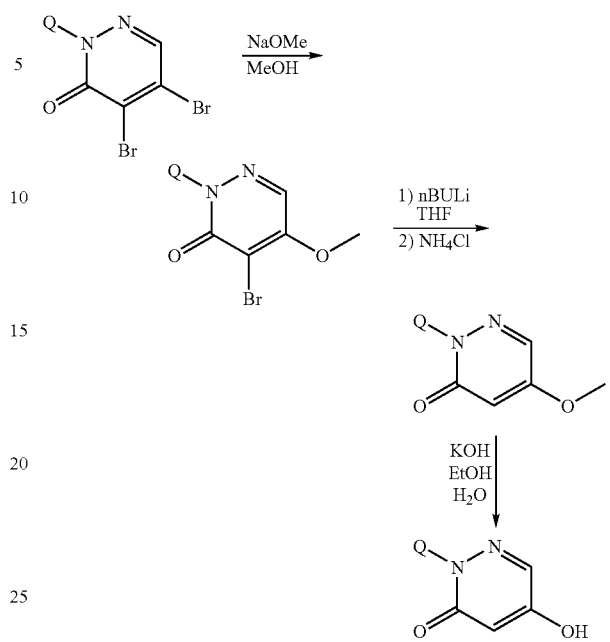

Example 30

2-(3,5-Dichlorophenyl)-5-hydroxypyridazin-3-one 2-(3,5-Dichlorophenyl)-5-methoxypyridazin-3-one (0.25 g, 0.92 mmoles) was suspended in ethanol (40 ml) and potassium hydroxide (0.12 g, 1.8 mmoles) was added in water (5 ml). Refluxed overnight with stirring to give a yellow solution. Evaporated to dryness and added 2M hydrochloric acid. Extracted with ethyl acetate (×2) and washed with water and dried over anhydrous magnesium sulphate. Filtered and evaporated to give a yellow solid. Triturated with dichloromethane to give a pale yellow solid. (0.1 g, 42%)

$^1$H NMR DMSOd6 δ 7.75 (d, 1H, J=3 Hz), 7.6 (m, 2H), 7.5 (m, 1H), 6.25 (d, 1H, J=3 Hz)

Also prepared in a similar manner

2-(2,5-Dichlorophenyl)-5-hydroxypyridazin-3-one

1H NMR DMSOd6 δ 10.9 (br s, 1H), 7.7 (d, 1H, J=3 Hz), 7.4 (m, 1H), 7.35 (m, 1H), 7.3 (m, 1H), 6.2 (d, 1H, J=3 Hz)

Example 31

2-(3,5-Dichlorophenyl)-5-methoxypyridazin-3-one

4-Bromo-2-(3,5-dichlorophenyl)-5-methoxypyridazin-3-one (2.5 g, 0.0071 moles) was dissolved in THF (250 ml) and cooled to −50° under nitrogen. 1.6M n-Butyl lithium (6.7 ml, 0.011 moles) was added dropwise with stirring. Allowed to warm to −20° over 1 hour. Added 1 equivalent of 1.6M n-Butyl lithium (4.4 ml, 0.0071 moles) dropwise. Stirred at −20° for 30 minutes. Poured into ammonium chloride solution and stirred for 15 minutes. Extracted with EtOAc (×2) and washed with water. Dried over anhydrous magnesium sulphate, filtered and evaporated to give a brown solid. (3.0 g) Purified using MPLC (silica, eluted with dichloromethane: EtOAc 9:1) to give a yellow solid. (0.25 g, 13%) Not pure used directly in the next reaction.

¹H NMR DMSOd6 δ 7.7 (d, 1H, J=3 Hz), 7.6 (d, 2H, J=2 Hz), 7.5 (d, 1H, J=2 Hz), 6.2 (d, 1H, J=3 Hz)

Also prepared in a similar manner 2-(2,5-Dichlorophenyl)-5-methoxypyridazin-3-one ¹H NMR DMSOd6 δ 7.95 (d, 1H, J=3 Hz), 7.75 (d, 1H, J=2.5 Hz), 7.7 (d, 1H, J=8 Hz), 7.6 (d, d, 1H, J=2.5, 8 Hz), 6.45 (d, 1H, J=3 Hz)

Example 32

4-Bromo-2-(3,5-dichlorophenyl)-5-methoxypyridazin-3-one

Sodium (0.28 g, 0.012 moles) was dissolved in methanol (100 ml) and a suspension of 4,5-Dibromo-2-(3,5-dichlorophenyl)pyridazin-3-one (4.0 g, 0.01 moles) in methanol (60 ml) was added. Refluxed overnight. Evaporated to dryness and added water. Filtered off the solid and dried in a dessicator. Triturated with ether and dried in a dessicator. (3.1 g, 89%)

¹H NMR DMSOd6 δ 8.35 (s, 1H), 7.75 (m, 1H), 7.7 (m, 2H), 4.15 (s, 3H)

Also prepared in a similar manner

4-Bromo-2-(2,5-dichlorophenyl)-5-methoxypyridazin-3-one

¹H NMR DMSOd6 δ 8.35 (s, 1H), 7.8 (d, 1H, J=2.5 Hz), 7.7 (d, 1H, J=8.5 Hz), 7.65 (d of d, 1H, J=2.5, 8 Hz), 4.15 (s, 3H)

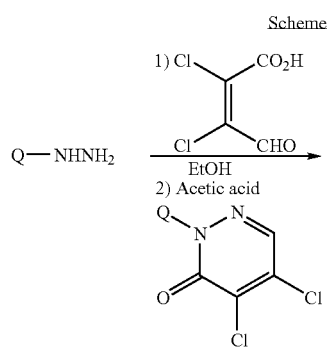

Scheme

Example 33

4-Chloro-2-phenyl-5-hydroxypyridazin-3-one 4,5-Dichloro-2-phenylpyridazin-3-one (2.4 g, 0.01 moles) was suspended in ethanol (50 ml) and potassium hydroxide (2.0 g, 0.03 moles) was added in water (20 ml). Refluxed for 4 hours. Evaporated to dryness and added water. Acidified to pH2 with c. hydrochloric acid. Filtered off the product as a buff solid and dried in a desiccator. (2.1 g) Took 0.5 g and dissolved in methanol, filtered and evaporated. Triturated with ether to give the product as a cream solid. (0.4 g, 76%)

¹H NMR DMSOd6 δ 7.9, (s, 1H), 7.5 (m, 4H), 7.4 (m, 1H)

Example 34

4,5-Dichloro-2-phenylpyridazin-3-one

Mucochloric acid (9.3 g, 0.055 moles) was dissolved in ethanol (60 ml) and phenyl hydrazine (5.4 g, 0.05 moles) was added. The reaction mixture was stirred at room temperature for 2 hours. Evaporated to a low bulk and the residue was suspended in glacial acetic acid (60 ml). Refluxed with stirring for 3 hours. Evaporated to dryness and triturated with methanol to give the required product as a pale brown solid. (11.0 g, 91%)

¹H NMR DMSOd6 δ 7.95 (s, 1H), 7.5 (m, 4H), 7.4 (m, 1H)

The following compounds have also been found to be effective in treating glaucoma or ocular hypertension according to the method of the present invention.

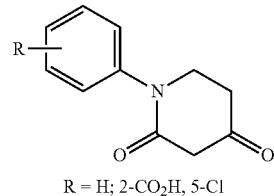

R = H; 2-CO₂H, 5-Cl

H Nishino et al. Tetrahedron, 2005, 11107-11124
H Nishino et al. Heterocyclic Comm. 2005, 11, 379-384
Bekhli et al. Chem. Heterocyclic Compds. Engl. Trans. 1970, 6, 814

Cyclohexane-1,3-diones

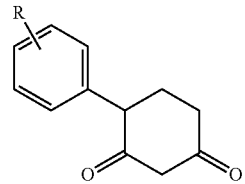

R = H, 4-OMe See EP 291114 (R = H, 4-OMe), U.S. 4546104, US 4795488 (R = 2-F)
Bergmann et al. J. Am. Chem. Soc. 1953, 3226
R = 3,4-DiOMe See Synthesis 1980, 394-397
R = 4-Cl See J. Med. Chem. 1981, 1006-1010

Pyridazin-3-ones

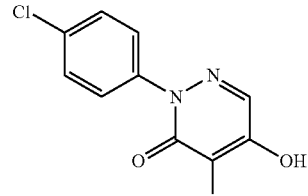

Nissan, EP 210647
R2 = H, Cl

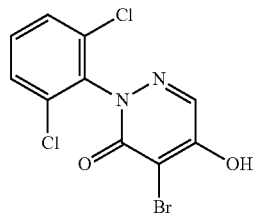

Pharmacia, WO2005007632

-continued

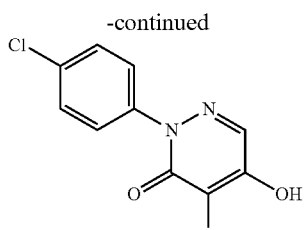

Nissan, EP 210647
R2 = H, Cl

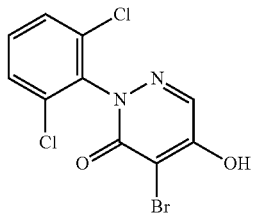

Pharmacia, WO2005007632

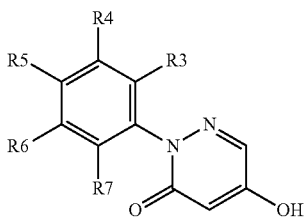

i) R3, R4, R5, R6, R7 = H
ii) R3 = CF₃, R4-R7 = H
iii) R4 = CF₃, R3, R5-R7 = H
iv) R5 = Cl, R3, R4, R6, R7 = H
i) Maier et al. Helv. Chim. Acta. 1954, 37, 523
ii), iii), iv) J. Het. Chem. 1989, 26, 169-176;
J. Het. Chem. 1990, 27, 471-477
i) R3, R4, R5, R6, R7 = H
iii) R4 = CF₃, R3, R5-R7 = H
ii) R4 = CF₃, R3, R5-R7 = H; iv) R5 = Cl, R3, R4, R6, R7 = H

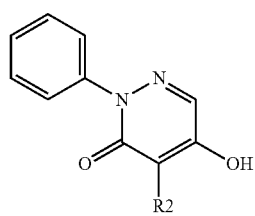

R2 = OMe  Chem. Pharm. Bull. 1971, 1635
1972, 747
R2 = SEt  Collect. Czech. Chem. Comm. 1980, 45, 127

It is apparent to one of ordinary skill in the art that different pharmaceutical compositions may be prepared and used with substantially the same results. That is, other Abnormal Cannabidiols will effectively lower intraocular pressure in animals and are within the scope of the present invention. Also, the novel compounds of the present invention may be used in a method of providing neuroprotection to the eye of a mammal in a similar manner to the abnormal Cannabidiols of Published U.S. Patent Application 2005/0282912.

The invention claimed is:

1. An ophthalmic solution comprising a therapeutically effective amount of a compound of formula I'

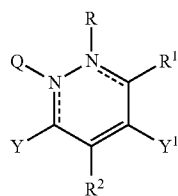

wherein R is selected from the group consisting of H, halogen; and $C_{1-5}$ alkyl;

$R^1$ is selected from the group consisting of H or halogen;

$R^2$ is independently selected from the group consisting of H, $C_{1-5}$ alkyl, halogen, $XC_{1-5}$ alkyl, $C_{1-5}$ alkylOR$^{13}$, $C_{1-5}$ alkylN(R$^{13}$)$_2$, N(R$^{13}$)$_2$, $XC_{1-5}$ alkylN(R$^{13}$)$_2$ and $XC_{1-5}$ alkylOR$^{13}$; X is O or S(O)$_n$; n is 0 or an integer of from 1 to 2;

Y is selected from the group consisting of keto and hydroxyl;

$Y^1$ is selected from the group consisting of hydroxyl, halogen and $C_1$-$C_5$ alkyl; and Q is a halogen-substituted phenyl, $R^{13}$ is selected from the group consisting of H, $C_{1-5}$ alkyl and $C_{3-8}$ cyclic alkyl.

2. The ophthalmic solution of claim 1, wherein said compound is 2-(4-Chlorophenyl)-5-hydroxypyridazin-3-one.

3. The ophthalmic solution of claim 1, wherein said compound is 2-(3,5-Difluorophenyl)-5-hydroxypyridazin-3-one.

4. The ophthalmic solution of claim 1, wherein said compound is 2-(2,5-Difluorophenyl)-5-hydroxypyridazin-3-one.

5. The ophthalmic solution of claim 1, wherein said compound is 2-(3,5-Dichlorophenyl)-5-hydroxypyridazin-3-one.

6. The ophthalmic solution of claim 1, wherein said compound is 2-(2,5-Dichlorophenyl)-5-hydroxypyridazin-3-one.

7. The ophthalmic solution of claim 1, wherein said compound is 4,5-Dichloro-2-phenylpyridazin-3-one.

8. The ophthalmic solution of claim 1, wherein said compound is 4,5-Dibromo-2-(3,5-difluorophenyl)pyridazin-3-one.

9. The ophthalmic solution of claim 1, wherein said compound is 4,5-Dibromo-2-(2,5-difluorophenyl)pyridazin-3-one.

10. The ophthalmic solution of claim 1, wherein said compound is 4,5-Dibromo-2-(2,5-dichlorophenyl)pyridazin-3-one.

11. The ophthalmic solution of claim 1, wherein said compound is 2-(3,5-Dichlorophenyl)-5-methoxypyridazin-3-one.

12. The ophthalmic solution of claim 1, wherein said compound is 2-(2,5-Dichlorophenyl)-5-methoxypyridazin-3-one.

13. The ophthalmic solution of claim 1, wherein said compound is 4-Bromo-2-(3,5-dichlorophenyl)-5-methoxypyridazin-3-one.

14. The ophthalmic solution of claim 1, wherein said compound is 4-Bromo-2-(2,5-dichlorophenyl)-5-methoxypyridazin-3-one.

15. The ophthalmic solution of claim 1, wherein said compound is 5-Hydroxy-2-(3-trifluoromethylphenyl)-pyridazin-3-one.

16. The ophthalmic solution of claim 1, further comprising at least one ingredient selected from the group of an ophthalmically acceptable preservative, buffer system, antioxidant and chelating agent.

17. A pharmaceutical product, comprising a container adapted to dispense its contents in metered form, and the ophthalmic solution of claim 16.

18. An ophthalmic solution comprising 5-Hydroxy-2-phenyl-pyridazin-3-one.

19. The ophthalmic solution of claim 1, wherein said compound is 4-Bromo-2-(3,5-dichlorophenyl)-5-hydroxypyridazin-3-one.

20. An ophthalmic solution comprising a therapeutically effective amount of a compound of formula I'

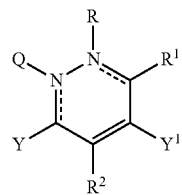

I' wherein R is selected from the group consisting of H, halogen; and $C_{1-5}$ alkyl;

$R^1$ is H;

$R^2$ is independently selected from the group consisting of H, $C_{1-5}$ alkyl, halogen, $C_{1-5}$alkylOR$^{13}$, $C_{1-5}$ alkylN($R^{13}$)$_2$, OC$_{1-5}$ alkylN($R^{13}$)$_2$, OC$_{1-5}$ alkylOR$^{13}$, and N($R^{14}$)$_2$;

$R^{13}$ is selected from the group consisting of H, $C_{1-5}$ alkyl and $C_{3-8}$ cyclic alkyl;

$R^{14}$ is selected from the group consisting of $C_{1-5}$ alkyl and $C_{3-8}$ cyclic alkyl;

Y is selected from the group consisting of keto and hydroxyl;

$Y^1$ is selected from the group consisting of hydroxyl, halogen and $C_1$-$C_5$ alkyl; and Q is phenyl.

21. The ophthalmic solution of claim 20, wherein said compound is 4-Chloro-2-phenyl-5-hydroxy-pyridazin-3-one.

22. The ophthalmic solution of claim 20, further comprising at least one ingredient selected from the group of an ophthalmically acceptable preservative, buffer system, antioxidant and chelating agent.

23. A pharmaceutical product, comprising a container adapted to dispense its contents in metered form, and the ophthalmic solution of claim 22.

24. An ophthalmic solution comprising a therapeutically effective amount of a compound of formula I'

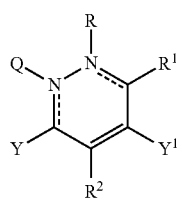

I' wherein R is selected from the group consisting of H, halogen; and $C_{1-5}$ alkyl;

$R^1$ is selected from the group consisting of H or halogen;

$R^2$ is independently selected from the group consisting of H, $C_{1-5}$ alkyl, halogen, XC$_{1-5}$ alkyl, $C_{1-5}$ alkylOR$^{13}$, $C_{1-5}$ alkylN($R^{13}$)$_2$, N($R^{13}$)$_2$, XC$_{1-5}$ alkylN($R^{13}$)$_2$ and XC$_{1-5}$ alkylOR$^{13}$; X is O or S(O)$_n$; n is 0 or an integer of from 1 to 2;

Y is selected from the group consisting of keto and hydroxyl;

$Y^1$ is selected from the group consisting of hydroxyl, halogen and $C_1$-$C_5$ alkyl; and Q is a compound having the formula

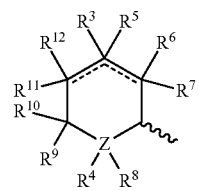

wherein a dotted line represents the presence or absence of a double bond and the wavy line represents a direct bond;

Z is N or C;

$R^3$ is selected from the group consisting of H, hydroxyl, oxo, $C_{1-5}$ alkyl, $C_{1-5}$ alkylOR$^{13}$ and $C_{is}$ alkylN($R^{13}$)$_2$;

$R^4$ is selected from the group consisting of H, $C_{1-5}$ alkenyl, $C_{1-5}$ alkyl, $C_{1-5}$ alkylOR$^{13}$ and $C_{1-5}$ alkylN($R^{13}$)$_2$;

$R^5$, $R^6$, $R^7$, $R^8$, $R^9$, $R^{10}$, $R^{11}$, and $R^{12}$ are independently selected from the group consisting of H, $C_{1-5}$ alkyl, $C_{1-5}$ alkylOR$^{13}$ and OR$^{13}$;

$R^{13}$ is selected from the group consisting of H, $C_{1-5}$ alkyl and $C_{3-8}$ cyclic alkyl.

25. The ophthalmic solution of claim 24, further comprising at least one ingredient selected from the group of an ophthalmically acceptable preservative, buffer system, antioxidant and chelating agent.

26. A pharmaceutical product, comprising a container adapted to dispense its contents in metered form, and the ophthalmic solution of claim 25.

27. An ophthalmic solution comprising a therapeutically effective amount of a compound selected from the group 4-Bromo-2-(3,5-difluorophenyl)-5-hydroxypyridazin-3-one, 4-Bromo-2-(2,5-difluorophenyl)-5-hydroxypyridazin-3-one, and 4-Bromo-2-(2,5-dichlorophenyl)-5-hydroxypyridazin-3-one.

28. The ophthalmic solution of claim 27, further comprising at least one ingredient selected from the group of an ophthalmically acceptable preservative, buffer system, antioxidant and chelating agent.

29. A pharmaceutical product, comprising a container adapted to dispense its contents in metered form, and the ophthalmic solution of claim 27.

* * * * *

UNITED STATES PATENT AND TRADEMARK OFFICE
CERTIFICATE OF CORRECTION

PATENT NO. : 7,968,711 B2
APPLICATION NO. : 11/739183
DATED : June 28, 2011
INVENTOR(S) : June Chen et al.

It is certified that error appears in the above-identified patent and that said Letters Patent is hereby corrected as shown below:

On page 2, in column 1, under "Other Publications", line 33, delete "Pyr Idazines" and insert -- Pyridazines --, therefor.

On page 2, in column 2, under "Other Publications", line 14, delete "Thiophospornic" and insert -- Thiophosphoric --, therefor.

On page 2, in column 2, under "Other Publications", line 19, delete "andController" and insert -- and Controller --, therefor.

On page 2, in column 2, under "Other Publications", line 23, delete "actic" and insert -- acetic --, therefor.

On page 2, in column 2, under "Other Publications", line 24, delete "chlorophyenylamino)" and insert -- chlorophenylamino) --, therefor.

On page 2, in column 2, under "Other Publications", line 25, delete "andits" and insert -- and its --, therefor.

On page 2, in column 2, under "Other Publications", line 25, delete "Chmistry" and insert -- Chemistry --, therefor.

On page 2, in column 2, under "Other Publications", line 34, delete "Sandmyer" and insert -- Sandmeyer --, therefor.

On page 2, in column 2, under "Other Publications", line 38, delete "inhibitorof" and insert -- inhibitor of --, therefor.

In column 1, line 40-41, delete "pupilary" and insert -- pupillary --, therefor.

In column 3, line 40, delete "$C(R^{11}1)$" and insert -- $C(R^{11})$ --, therefor.

In column 9, line 55, delete "q.s" and insert -- q.s. --, therefor.

In column 10, line 41, delete "dextrophan," and insert -- dextrorphan, --, therefor.

Signed and Sealed this
Third Day of July, 2012

David J. Kappos
*Director of the United States Patent and Trademark Office*

CERTIFICATE OF CORRECTION (continued)
U.S. Pat. No. 7,968,711 B2

In column 10, line 51, delete "chlorostenol," and insert -- cloprostenol, --, therefor.

In column 10, line 52, delete "chlorostenol," and insert -- cloprostenol, --, therefor.

In column 10, line 61-62, delete "pneumatonometry" and insert -- pneumatonometer --, therefor.

In column 12, line 15, delete "H)," and insert -- 1H), --, therefor.

In column 14, line 63-67, delete "(4.0 g). Dissolved in dichloromethane and washed with 2M hydrochloric acid. Washed with water and dried over anhydrous magnesium sulphate. The solvent was removed by evaporation under reduced pressure to give the product as a brown oil (1.3 g)." and insert the same on Col. 14, Line 62, after "oil" as a continuation of the same paragraph.

In column 16, line 7, delete "??1.7" and insert -- $\delta$ 1.7 --, therefor.

In column 16, line 13, delete "dihydropyidine" and insert -- dihydropyridine --, therefor.

In column 16, line 14, delete "?" and insert -- $\delta$ --, therefor.

In column 16, line 36, delete "$\delta$?1.55" and insert -- $\delta$ 1.55 --, therefor.

In column 16, line 66, delete "??1.67" and insert -- $\delta$ 1.67 --, therefor.

In column 17, line 22, delete "$\delta$?1.6" and insert -- $\delta$ 1.6 --, therefor.

In column 17, line 25, delete "piperidine2," and insert -- piperidine-2, --, therefor.

In column 19, line 11, delete "CDCl$_3$, ppm)" and insert -- (CDCl$_3$, ppm) --, therefor.

In column 19, line 24, delete "CDCl$_3$, ppm)" and insert -- (CDCl$_3$, ppm) --, therefor.

In column 21, line 13, delete "$^1$NMR" and insert -- $^1$H NMR --, therefor.

In column 21, line 29, delete "1H NMR" and insert -- $^1$H NMR --, therefor.

In column 22, line 59, delete "1H NMR" and insert -- $^1$H NMR --, therefor.

In column 24, line 48, delete "1H NMR" and insert -- $^1$H NMR --, therefor.

In column 30, line 30, in claim 24, delete "C$_{is}$" and insert -- C$_{1-5}$ --, therefor.